US008734767B2

(12) United States Patent
Johnson et al.

(10) Patent No.: US 8,734,767 B2
(45) Date of Patent: May 27, 2014

(54) AMINOFUNCTIONAL ENDBLOCKED SILICONE POLYETHER COPOLYMERS IN PERSONAL CARE COMPOSITIONS

(75) Inventors: Bethany Johnson, Midland, MI (US); John Joseph Kennan, Nonthaburi (TH); Kevin Lewis, Sanford, MI (US)

(73) Assignee: Dow Corning Corporation, Midland, MI (US)

( * ) Notice: Subject to any disclaimer, the term of this patent is extended or adjusted under 35 U.S.C. 154(b) by 315 days.

(21) Appl. No.: 13/124,573

(22) PCT Filed: Oct. 13, 2009

(86) PCT No.: PCT/US2009/060435
§ 371 (c)(1),
(2), (4) Date: Apr. 15, 2011

(87) PCT Pub. No.: WO2010/047993
PCT Pub. Date: Apr. 29, 2010

(65) Prior Publication Data
US 2011/0200548 A1    Aug. 18, 2011

Related U.S. Application Data

(60) Provisional application No. 61/107,422, filed on Oct. 22, 2008.

(51) Int. Cl.
*A61K 8/898* (2006.01)
*A61Q 5/00* (2006.01)
*C08G 77/38* (2006.01)

(52) U.S. Cl.
CPC ............... *A61K 8/898* (2013.01); *C08G 77/38* (2013.01); *A61Q 5/00* (2013.01)
USPC ..................................... 424/70.122; 514/474

(58) Field of Classification Search
None
See application file for complete search history.

(56) References Cited

U.S. PATENT DOCUMENTS

| | | | |
|---|---|---|---|
| 2,798,053 A | 7/1957 | Brown | |
| 3,389,160 A | 6/1968 | Reid | |
| 3,419,593 A | 12/1968 | Willing | |
| 3,715,334 A | 2/1973 | Karstedt | |
| 3,814,730 A | 6/1974 | Karstedt | |
| 3,923,705 A | 12/1975 | Smith | |
| 3,928,558 A | 12/1975 | Cheesman et al. | |
| 3,958,581 A | 5/1976 | Abegg et al. | |
| 3,962,418 A | 6/1976 | Birkofer | |
| 4,009,256 A | 2/1977 | Nowak, Jr. et al. | |
| 4,122,029 A | 10/1978 | Gee et al. | |
| 4,704,272 A | 11/1987 | Oh et al. | |
| 4,741,855 A | 5/1988 | Grote et al. | |
| 4,788,006 A | 11/1988 | Bolich, Jr. et al. | |
| 5,175,325 A | 12/1992 | Brown et al. | |
| 5,387,417 A | 2/1995 | Rentsch | |
| 5,389,364 A | 2/1995 | Cifuentes et al. | |
| 5,409,695 A | 4/1995 | Abrutyn et al. | |
| 5,419,627 A | 5/1995 | Oldinski | |
| 5,504,149 A | 4/1996 | Kosal | |
| 5,688,889 A | 11/1997 | Canivenc et al. | |
| 5,807,956 A | 9/1998 | Czech | |
| 5,811,487 A | 9/1998 | Schulz, Jr. et al. | |
| 5,919,441 A | 7/1999 | Mendolia et al. | |
| 5,981,680 A | 11/1999 | Petroff et al. | |
| 5,981,681 A | 11/1999 | Czech | |
| 6,013,682 A | 1/2000 | Dalle et al. | |
| 6,048,519 A | 4/2000 | Hiraishi et al. | |
| 6,051,216 A | 4/2000 | Barr et al. | |
| 6,187,891 B1 | 2/2001 | Rautschek et al. | |
| 6,197,876 B1 | 3/2001 | Policello et al. | |
| 6,589,519 B1 | 7/2003 | Restle et al. | |
| 6,610,280 B2 | 8/2003 | Ainger et al. | |
| 6,630,415 B2 | 10/2003 | Phillips et al. | |
| 6,835,419 B2 | 12/2004 | Herzig et al. | |
| 6,986,886 B2 | 1/2006 | Hammond et al. | |
| 2003/0072730 A1 | 4/2003 | Tournilhac | |
| 2003/0170188 A1 | 9/2003 | Ferrari et al. | |
| 2003/0235553 A1 | 12/2003 | Lu et al. | |
| 2004/0083553 A1 | 5/2004 | Chardon et al. | |
| 2004/0180032 A1 | 9/2004 | Manelski et al. | |
| 2007/0031365 A1 | 2/2007 | Terada | |
| 2010/0048795 A1* | 2/2010 | Kennan et al. ................ 524/500 |

FOREIGN PATENT DOCUMENTS

| | | |
|---|---|---|
| EP | 100861 | 9/1989 |
| EP | 0492657 | 1/1996 |
| EP | 0684041 | 4/1997 |
| EP | 0859590 | 12/2001 |
| EP | 1283472 | 8/2002 |
| EP | 1266648 | 12/2002 |
| EP | 1266653 | 12/2002 |
| EP | 1009366 | 3/2003 |
| EP | 1384467 | 7/2003 |
| EP | 0973487 | 11/2003 |
| EP | 0924239 | 11/2004 |
| EP | 0824563 | 6/2005 |
| EP | 1266647 | 5/2007 |
| EP | 1754467 | 5/2009 |
| EP | 1744815 | 1/2010 |
| EP | 1432753 | 7/2010 |
| JP | 1991269570 | 12/1991 |
| JP | 1997183854 | 7/1997 |
| JP | 2002326914 | 11/2002 |
| WO | WO9522311 | 8/1995 |
| WO | WO9922311 | 5/1999 |
| WO | WO0247632 | 6/2002 |

(Continued)

OTHER PUBLICATIONS

Wendel et al, Organofunctional Silicones for Personal Care Applications. Cosmetics & Toiletries 98, 103-106 (1983).

*Primary Examiner* — Ernst V Arnold
(74) *Attorney, Agent, or Firm* — Alan Zombeck

(57) ABSTRACT

Personal care compositions containing aminofunctional endblocked silicone polyether copolymers are disclosed. The aminofunctional endblocked silicone polyether copolymers are particularly useful in hair care formulations to provide conditioning, which includes ease of detangling, combing, pliability, smoothness, slipperiness and styling benefits.

6 Claims, No Drawings

(56) References Cited

FOREIGN PATENT DOCUMENTS

| WO | WO03101412 | 12/2003 |
| WO | WO03105789 | 12/2003 |
| WO | WO03106614 | 12/2003 |
| WO | WO2004000247 | 12/2003 |
| WO | WO2004054523 | 7/2004 |
| WO | WO2004054524 | 7/2004 |
| WO | WO2004060101 | 7/2004 |
| WO | WO2004060271 | 7/2004 |
| WO | WO2004060276 | 7/2004 |
| WO | WO2005103117 | 11/2005 |
| WO | WO2008127519 | 10/2008 |

* cited by examiner

AMINOFUNCTIONAL ENDBLOCKED SILICONE POLYETHER COPOLYMERS IN PERSONAL CARE COMPOSITIONS

CROSS REFERENCE TO RELATED APPLICATIONS

This application is a U.S. national stage filing under 35 U.S.C. §371 of PCT Application No. PCT/US09/60435 filed on Oct. 13, 2009, currently pending, which claims the benefit of U.S. Provisional Patent Application No. 61/107,422 filed Oct. 22, 2008 under 35 U.S.C. §119 (e). PCT Application No. PCT/US09/60435 and U.S. Provisional Patent Application No. 61/107,422 are hereby incorporated by reference.

TECHNICAL FIELD

This disclosure relates to personal care products containing aminofunctional endblocked silicone polyether copolymers. Emulsions of the aminofunctional endblocked silicone polyether block copolymers are particularly useful in hair care formulations to provide conditioning, which includes ease of detangling, combing, pliability, smoothness, slipperiness and styling benefits.

BACKGROUND

In today's hair care market, there are unmet needs for conditioning and styling benefits in hair care compositions. The present inventors have discovered that emulsions containing certain silicone amino polyether block copolymers are useful for imparting conditioning and styling benefits to hair. In particular, the present inventors have found the emulsions of the silicone amino polyether block copolymers disclosed in PCT/US08/002,962 provide such benefits. That is, hair care compositions containing these emulsions demonstrate smoothness, pliability and slipperiness. Furthermore, the perception of moisturization, wet and dry combing benefits, as well as flexible styling benefits are imparted to hair treated with the present compositions.

SUMMARY

The present disclosure relates personal care compositions containing a silicone polyether copolymer having the average formula;

$$A-R_2SiO(R_2SiO)_xSiR_2-[[R^1O(C_mH_{2m}O)_yR^1][R_2SiO(R_2SiO)_x]R_2Si]_n-A$$

where
A is an aminofunctional endblocking group of the formula $R^A CH_2CH(OH)CH_2OR^2-$ wherein $R^A$ is an aminofunctional group,
x is ≥0, m is from 2 to 4 inclusive, y is ≥4, n is ≥1,
R is independently a monovalent hydrocarbon group containing 1 to 30 carbons,
$R^1$ is a divalent hydrocarbon containing 2 to 30 carbons.

Representative personal care compositions include; a shampoo, a hair conditioner, a hair fixative, a hair styling aid, a hair colorant, a hair relaxer, a shower gel, a skin moisturizer, a skin conditioner and a body conditioner. The silicone amino polyether block copolymer emulsions are particularly useful for imparting conditioning, which includes ease of detangling, combing, pliability, smoothness, and slipperiness and styling benefits to hair.

DETAILED DESCRIPTION

The aminofunctional endblocked silicone polyether copolymers useful in the personal care composition of the present disclosure may be selected from any of those as disclosed in PCT/US08/002,962, which is hereby incorporated by reference for its teaching of aminofunctional endblocked silicone polyether copolymers and emulsions thereof.

The silicone polyether copolymers of the present disclosure are block copolymers having repeating units of a divalent organic group containing at least one polyether group as one block, and a diorganopolysiloxane as the other block, represented as $[[R^1O(C_mH_{2m}O)_yR^1][R_2SiO(R_2SiO)_x]R_2Si]_n$. The subscript n represents on average the number repeating units in the copolymer, and n is ≥1, alternatively n ranges from 1 to 50.

The divalent organic group in the silicone polyether copolymers of the present disclosure comprises at least one polyether group. As used herein, "polyether" designates a polyoxyalkylene group. The polyoxyalkylene group may be represented by, although not limited to, the formula $(C_mH_{2m}O)_y$ wherein m is from 2 to 4 inclusive, and y is greater than 4, alternatively y may range from 5 to 60, or alternatively from 5 to 30. The polyoxyalkylene group may comprise oxyethylene units $(C_2H_4O)$, oxypropylene units $(C_3H_6O)$, oxybutylene units $(C_4H_8O)$, or mixtures thereof. Typically, the polyoxyalkylene group comprises oxyethylene units $(C_2H_4O)$ or mixtures of oxyethylene units and oxypropylene units.

The "silicone" group in the silicone polyether copolymers of the present disclosure is a diorganopolysiloxane. The diorganopolysiloxane may be a predominately linear siloxane polymer having the formula $(R_2SiO)_x$, wherein R is independently selected from a monovalent hydrocarbon group, x is ≥1, alternatively x may range from 2 to 100, or from 2 to 50. The hydrocarbon groups represented by R in the siloxane polymer are free of aliphatic unsaturation. These organic groups may be independently selected from monovalent hydrocarbon and monovalent halogenated hydrocarbon groups free of aliphatic unsaturation. These monovalent groups may have from 1 to 30 carbon atoms, alternatively 1 to 10 carbon atoms, and are exemplified by, but not limited to alkyl groups such as methyl, ethyl, propyl, butyl, pentyl, hexyl, heptyl, octyl, undecyl, and octadecyl; cycloalkyl such as cyclohexyl; aryl such as phenyl, tolyl, xylyl, benzyl, and 2-phenylethyl; and halogenated hydrocarbon groups such as 3,3,3-trifluoropropyl, 3-chloropropyl, and dichlorophenyl. Typically, the diorganopolysiloxane is a predominately linear polydimethylsiloxane having the formula $(Me_2SiO)_x$, where x is as defined above.

At least one end of each polyether block is linked to an organopolysiloxane block by a divalent hydrocarbon group, designated $R^1$. This linkage is determined by the reaction employed to prepare the $(AB)_n$ block silicone polyether copolymer. The divalent hydrocarbon group $R^1$ may be independently selected from divalent hydrocarbon groups containing 2 to 30 carbons. Representative, non-limiting examples of such divalent hydrocarbon groups include; ethylene, propylene, butylene, isobutylene, pentylene, hexylene, heptylene, octylene, and the like. Representative, non-limiting examples of such divalent organofunctional hydrocarbons groups include acrylate and methacrylate. Typically, $R^1$ is isobutylene ($-CH_2CH(CH_3)CH_2-$).

The aminofunctional endblocking group A may have the formula $R^ACH_2CH(OH)CH_2OR^2-$ where $R^A$ is a monovalent amine functional group and $R^2$ is a divalent hydrocarbon linking group containing 2 to 6 carbon atoms, such as a divalent alkylene like ethylene, propylene, butylene, isobutylene, pentylene, or hexylene. Typically, $R^2$ is propylene $-CH_2CH_2CH_2-$. The monovalent amine functional group $R^4$ may be any amine functional organic group. The nitrogen atom of the amine functional group is bonded to the methylene group of the —CH$_2$CH(OH)CH$_2$OR$^2$— endblocking group. The amine functional group may be any secondary, tertiary, or quaternary amine, but typically are tertiary amines. The amine functional group may be include other organic functional groups, such as amino, hydroxy, epoxy, ether, amido, and carboxyl groups. Thus, $R^4$ may have the formula $(R^3)_2N$—, $H(R^3)N$—, or $(R^3)_3N$—, wherein $R^3$ is independently a monovalent organic containing 1 to 30 carbon atoms. Alternatively, $R^3$ is independently a monovalent hydrocarbon group containing 1 to 30 carbon atoms, such as alkyl groups containing 1 to 30 carbons like methyl, ethyl, propyl, butyl, and similar homologs. Representative, non limiting examples include; $(CH_3)HN$—, $(CH_3)_2N$—, $(CH_3CH_2)HN$—, $(CH_3CH_2)_2N$—, $(CH_3CH_2)_3N$—, $(HOCH_2CH_2)_2N$—, and $[CH_2CH(OH)CH_3]_2N$—. The amine functional group may include cyclic amines such as; pyrrolidine; piperidine; piperazine; morpholine; 3-pyrrolidinol; 2,5-dimethylpyrrolidine; 1-methylpiperazine; 4-hydroxypiperidine; N-(2-hydroxyethyl)piperazine, 2,6-dimethylpiperidine; 1-ethylpiperazine; 1-amine-4-methylpiperazine; and isoindoline.

In a further embodiment, the aminofunctional endblocking group A may have the formula,

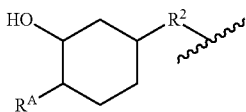

where $R^4$ and $R^2$ are the same as described above.

Representative, non-limiting, average formulas of the amine terminal silicone polyethers of the present disclosure are shown below;

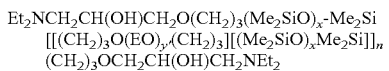

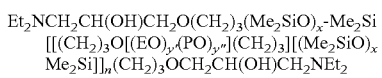

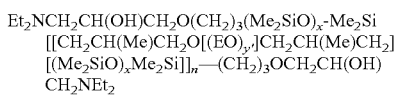

Et$_2$NCH$_2$CH(OH)CH$_2$O(CH$_2$)$_3$(Me$_2$SiO)$_x$-Me$_2$Si
[[CH$_2$CH(Me)CH$_2$O[(EO)$_{y'}$(PO)$_{y''}$]CH$_2$CH(Me)CH$_2$][(Me$_2$SiO)$_x$Me$_2$Si]]$_n$—(CH$_2$)$_3$OCH$_2$CH(OH)CH$_2$NEt$_2$ wherein
n and x are as defined above,
y' is ≥0, alternatively y' is 0 to 60,
y" is ≥0, alternatively y" is 0 to 60,
with the proviso that y'+y"≥4
Me is methyl, Et is ethyl,
EO is CH$_2$CH$_2$O, and
PO is CH$_2$CH(Me)O or CH$_2$CH$_2$CH$_2$O.

The aminofunctional endblocked silicone polyether block copolymers may be prepared by:
I) reacting;
A) a polyoxyalkylene having an unsaturated hydrocarbon group at each molecular terminal
B) a SiH terminated organopolysiloxane,
C) a hydrosilylation catalyst,
D) an optional solvent,
where the molar ratio of B/A is greater than one,
II) further reacting the product of step I with;
E) an epoxide having at least one aliphatic unsaturated hydrocarbon group to form an epoxide terminal silicone polyether block copolymer,
III) reacting the epoxide terminal silicone polyether block copolymer with
F) an amine compound
to form the amine terminal silicone polyether block copolymer.

Step I) in the above process involves reacting ingredients A) a polyoxyalkylene having an unsaturated hydrocarbon group at each molecular terminal, B) a SiH terminated organopolysiloxane, C) a hydrosilylation catalyst, and D) an optional solvent, where the molar ratio of B/A is greater than one.

A) The Polyoxyalkylene

The polyoxyalkylene useful in the process of the present invention can be any polyoxyalkylene group that is terminated at each molecular chain end (i.e. alpha and omega positions) with a unsaturated organic group. The polyoxyalkylene may result from the polymerization of ethylene oxide, propylene oxide, butylene oxide, 1,2-epoxyhexane, 1,2-epoxyoctane, cyclic epoxides such as cyclohexene oxide or exo-2,3-epoxynorborane. Alternatively, the polyoxyalkylene may be represented by the formula $(C_mH_{2m}O)_y$, wherein m is from 2 to 4 inclusive, and y is greater than 4, alternatively y may range from 5 to 60, or alternatively from 5 to 30. The polyoxyalkylene group may comprise oxyethylene units (C$_2$H$_4$O), oxypropylene units (C$_3$H$_6$O), oxybutylene units (C$_4$H$_8$O), or mixtures thereof. Typically, the polyoxyalkylene group comprises oxyethylene units (C$_2$H$_4$O) or mixtures of oxyethylene units and oxypropylene units. The unsaturated organic group can be an unsaturated aliphatic hydrocarbon group such as alkenyl or alkynyl group. Representative, non-limiting examples of the alkenyl groups are shown by the following structures; H$_2$C=CH—, H$_2$C=CHCH$_2$—, H$_2$C=C(CH$_3$)CH$_2$—, H$_2$C=CHCH$_2$CH$_2$—, H$_2$C=CHCH$_2$CH$_2$CH$_2$—, and H$_2$C=CHCH$_2$CH$_2$CH$_2$CH$_2$— Representative, non-limiting examples of alkynyl groups are shown by the following structures; HC≡C—, HC≡CCH$_2$—, HC≡CC(CH$_3$)—, HC≡CC(CH$_3$)$_2$—, and HC≡CC(CH$_3$)$_2$CH$_2$—. Alternatively, the unsaturated organic group can be an organofunctional hydrocarbon such as an acrylate, methacrylate and the like.

The polyoxyalkylene may be selected from those having the average formula

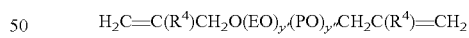

wherein
y' is ≥1, alternatively y' is 0 to 60,
y" is ≥0, alternatively y" is 0 to 60,
with the proviso that y'+y"≥4
$R^4$ is hydrogen or an alkyl group containing 1 to 20 carbon atoms,
EO is —CH$_2$CH$_2$O—,
PO is —CH$_2$CH(Me)O— or —CH$_2$CH$_2$CH$_2$O—.

Polyoxyalkylenes having an unsaturated aliphatic hydrocarbon group at each molecular terminal are known in the art, and many are commercially available.

Representative, non-limiting examples of polyoxyalkylenes include;

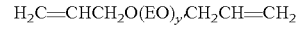

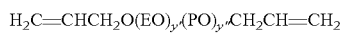

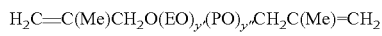

wherein
y' is ≥1, alternatively y' is 4 to 60,
y" is ≥0, alternatively y" is 0 to 60,
Me is methyl,
EO is —CH$_2$CH$_2$O—, and PO is —CH$_2$CH(Me)O— or —CH$_2$CH$_2$CH$_2$O—.

Polyoxyalkylenes having an unsaturated aliphatic hydrocarbon group at each molecular terminal are commercially available from NOF (Nippon Oil and Fat, Tokyo, Japan) and Clariant Corp. (Charlottesville, N.C.).

B) The SiH Terminated Organopolysiloxane

The SiH terminated organopolysiloxanes useful in the process of the present invention can be represented by the formula M'DM', where "M'" means a siloxane unit of formula R$_2$HSiO$_{1/2}$, "D" means a siloxane unit of formula R$_2$SiO$_{2/2}$, where R is independently a monovalent hydrocarbon group as defined above. Typically, the SiH terminated organopolysiloxane is a dimethylhydrogensiloxy-terminated polydimethylsiloxane having the average formula Me$_2$HSiO(Me$_2$SiO)$_x$SiHMe$_2$, where x is ≥1, alternatively x may range from 2 to 200, or from 50 to 150. SiH terminated organopolysiloxanes and methods for their preparation are well known in the art.

C) The Hydrosilylation Catalyst

The SiH terminated organopolysiloxane and polyoxyethylene having an unsaturated organic group at each molecular terminal are reacted in the presence of a hydrosilylation catalyst, which are known in the art. Hydrosilylations are well known in the art and involves the reaction between a polysiloxane containing ≡Si—H groups, and a material containing unsaturation, e.g., vinyl groups. The reaction typically uses a catalyst to effect the reaction between the ≡SiH containing polysiloxane and the material containing unsaturation. Suitable catalysts are Group VIII transition metals, i.e., the noble metals. Such noble metal catalysts are described in U.S. Pat. No. 3,923,705, incorporated herein by reference to show platinum catalysts. One preferred platinum catalyst is Karstedt's catalyst, which is described in Karstedt's U.S. Pat. Nos. 3,715,334 and 3,814,730, incorporated herein by reference. Karstedt's catalyst is a platinum divinyl tetramethyl disiloxane complex typically containing one weight percent of platinum in a solvent such as toluene. Another preferred platinum catalyst is a reaction product of chloroplatinic acid and an organosilicon compound containing terminal aliphatic unsaturation. It is described in U.S. Pat. No. 3,419,593, incorporated herein by reference. Most preferred as the catalyst is a neutralized complex of platinous chloride and divinyl tetramethyl disiloxane, for example as described in U.S. Pat. No. 5,175,325.

The noble metal catalyst can be used in an amount of from 0.00001-0.5 parts per 100 weight parts of the ≡SiH containing polysiloxane. Alternatively, the catalyst should be used in an amount sufficient to provide 0.1-15 parts per million (ppm) Pt metal per total composition.

D) The Optional Solvent

The hydrosilylation reaction can be conducted neat or in the presence of D), a solvent. The solvent can be an alcohol such as methanol, ethanol, isopropanol, butanol, or n-propanol, a ketone such as acetone, methylethyl ketone, or methyl isobutyl ketone; an aromatic hydrocarbon such as benzene, toluene, or xylene; an aliphatic hydrocarbon such as heptane, hexane, or octane; a glycol ether such as propylene glycol methyl ether, dipropylene glycol methyl ether, propylene glycol n-butyl ether, propylene glycol n-propyl ether, or ethylene glycol n-butyl ether, a halogenated hydrocarbon such as dichloromethane, 1,1,1-trichloroethane or methylene chloride, chloroform, dimethyl sulfoxide, dimethyl formamide, acetonitrile, tetrahydrofuran, white spirits, mineral spirits, or naphtha.

The amount of solvent can be up to 70 weight percent, but is typically from 20 to 50 weight percent, said weight percent being based on the total weight of components in the hydrosilylation reaction. The solvent used during the hydrosilylation reaction can be subsequently removed from the resulting silicone polyether by various known methods.

Step I) effects a hydrosilylation reaction, wherein the SiH units of ingredient B react with the unsaturated aliphatic hydrocarbon group of ingredient A to form an Si—C bond. The reaction may be conducted under those conditions known in the art for effecting hydrosilylations reactions.

Additional components can be added to the hydrosilylation reaction which are known to enhance such reactions. These components include salts such as sodium acetate which have a buffering effect in combination with platinum catalysts.

The amount of ingredients A and B used in step I may vary, providing the molar ratio of B/A is greater than 1, alternatively the molar ratio of B/A may vary from 1.05 to 2, alternatively from 1.2 to 2. Although, not wishing to be bound by any theory, the present inventors believe step I provides a reaction product comprising a silicone polyether [AB]$_n$ copolymer having terminal SiH units. These SiH units are further reacted in step II.

Step II) in the process of the present disclosure involves further reacting the product of step I with E) an epoxide having at least one aliphatic unsaturated hydrocarbon group to form an epoxide terminal silicone polyether block copolymer. The reaction in step II is another hydrosilylation reaction. Typically, the epoxide having at least one aliphatic unsaturated hydrocarbon group is simply added at the end of step I, and the second hydrosilylation reaction allowed to progress under the same conditions. Alternatively, additional amounts of the hydrosilylation catalyst C) may be added.

Representative, non-limiting examples of the epoxide having at least one aliphatic unsaturated group suitable for the reaction in step II include;
allyl glycidyl ether, CAS 106-92-3
vinylcyclohexene oxide, CAS 106-86-5
5,6-epoxy-1-hexene, (or 1,2-epoxy-5-hexene and 2-(3-butenyl)oxirane), CAS: 10353-53-4
9,10-epoxy-1 decene, (or 2-(7-octenyl)oxirane and 1,2-epoxy-9-decene) CAS: 85721-25-1
7,8-epoxy-1-octene, (or 1,2-epoxy-7-octene and 2-(5-hexenyl) oxirane) CAS: 19600-63-6
2-vinyloxirane, (or 3,4-epoxy-1-butene, butadiene monoxide) CAS: 930-22-3
2-methyl-2-vinyloxirane, (or Isoprene monoxide) CAS: 1838-94-4
Glycidyl acrylate, (or 2-oxiranylmethyl acrylate)
Glycidyl methacrylate, (or 2-oxiranylmethyl 2-methacrylate) CAS: 106-91-2
Limonene oxide, mixture of cis- and trans-, CAS: 1195-92-2)
Allyloxy-3,4-epoxytricyclo(5.2.1.0 2,6)decane, CAS: 2279-19-8.

The amount of the epoxide added in step II may vary, but is typically added in sufficient amount to consume the residual Si—H, that is a molar excess of epoxide to SiH is used. Lower amounts of the epoxide may be used if limiting free epoxide is desired, with the understanding that only partial endblocking will be achieved.

Step I) and Step II) may be carried out sequentially or simultaneously; however typically the reactions are conducted sequentially to build molecular weight of the (AB)$_n$ before consuming the final quantities of Si—H with an excess of the epoxy endcapping group.

Step III) in the process of the present disclosure involves reacting the epoxide terminal silicone polyether block copolymer formed in step II) with F) an amine compound to form the amine terminal silicone polyether block copolymer. Step III effects a ring opening reaction of the epoxide by the addition of an amine compound.

The amine compound may be any amine compound, but typically are secondary amines. The amine compound may be selected from an amine compound containing an $R^4$ group, where $R^4$ is as defined above. Thus, $R^4$ may have the formula $(R^3)_2N-$, $H(R^3)N-$, or $(R^3)_3N-$, wherein $R^3$ is independently a monovalent organic containing 1 to 30 carbon atoms. Alternatively, $R^3$ is independently a monovalent hydrocarbon group containing 1 to 30 carbon atoms, such as alkyl groups containing 1 to 30 carbons like methyl, ethyl, propyl, butyl, and similar homologs. The amine compound may include other organic functional groups, such as amino, hydroxy, epoxy, ether, amido, and carboxyl groups. Representative, non limiting examples include; $(CH_3)NH_2$, $(CH_3)_2NH$, $(CH_3CH_2)NH_2$, $(CH_3CH_2)_2NH$, $(CH_3CH_2)_3N$, $(HOCH_2CH_2)_2NH$, and $(CH_3CH(OH)CH_2)_2NH$.

The amine functional group may include cyclic amines. Representative non-limiting examples of suitable cyclic amines include;
1-(2-hydroxyethyl)piperazine,
piperazine,
Pyrrolidine, CAS: 123-75-1
Piperidine, CAS: 110-89-4
Morpholine, CAS: 110-91-8
3-Pyrrolidinol, CAS: 40499-83-0
2,5-dimethylpyrrolidine, CAS: 3378-71-0
1-methylpiperazine, CAS: 109-01-3
4-hydroxypiperidine, CAS: 5382-16-1
2,6-dimethylpiperidine, CAS: 504-03-0
1-ethylpiperazine, CAS: 5308-25-8
1-amine-4-methylpiperazine, CAS: 6928-85-4
Isoindoline, CAS: 496-12-8

The amine terminal silicone polyether block copolymers of the present disclosure may be an ingredient in an emulsion composition. As used herein, "emulsion" is meant to encompass water continuous emulsions (for example an oil in water type emulsion, or a silicone in water emulsion), oil or silicone continuous emulsions (water in oil emulsions or water in silicone emulsions), or multiple emulsions (water/oil/water, oil/water/oil types, water/silicone/water, or silicone/water/silicone). The amine terminal silicone polyether block copolymers of the present disclosure may be added to any type of emulsion by common mixing techniques. The addition the amine or quat terminal silicone polyether block copolymers may occur either during the preparation of the emulsion, or subsequently post added to a pre-formed emulsion. There are no special requirements or conditions needed to effect the mixing of amine terminal silicone polyether block copolymers of the present disclosure and the emulsion. Mixing techniques can be simple stirring, homogenizing, sonalating, and other mixing techniques known in the art to effect the formation of emulsions. The mixing can be conducted in a batch, semi-continuous, or continuous process.

The amount of amine terminal silicone polyether block copolymers of the present disclosure added to the emulsion can vary and is not limited, however the amounts typically may range from a silicone polyether copolymer/emulsion weight ratio of 0.1/99 to 99/0.1, alternatively 1/99 to 99/1.

The emulsions used may be w/o, w/s, or multiple phase emulsions using silicone emulsifiers. Typically the water-in-silicone emulsifier in such formulation is non-ionic and is selected from polyoxyalkylene-substituted silicones, silicone alkanolamides, silicone esters and silicone glycosides. Silicone-based surfactants may be used to form such emulsions and are well known in the art, and have been described for example in U.S. Pat. No. 4,122,029 (Gee et al.), U.S. Pat. No. 5,387,417 (Rentsch), and U.S. Pat. No. 5,811,487 (Schulz et al).

The emulsions containing the silicone polyether copolymer may contain anionic surfactants, cationic surfactants, and nonionic surfactants. The anionic surfactants include sulfonic acids and their salt derivatives. Some examples of anionic surfactants are alkali metal sulfosuccinates; sulfonated glyceryl esters of fatty acids such as sulfonated monoglycerides of coconut oil acids; salts of sulfonated monovalent alcohol esters such as sodium oleyl isothionate; amides of amino sulfonic acids such as the sodium salt of oleyl methyl tauride; sulfonated products of fatty acid nitriles such as palmitonitrile sulfonate; sulfonated aromatic hydrocarbons such as sodium alpha-naphthalene mono sulfonate; condensation products of naphthalene sulfonic acids with formaldehyde; sodium octahydro anthracene sulfonate; alkali metal alkyl sulfates; ether sulfates having alkyl groups of eight or more carbon atoms such as sodium lauryl ether sulfate; and alkylaryl sulfonates having one or more alkyl groups of eight or more carbon atoms such as neutral salts of hexadecylbenzene sulfonic acid and $C_{20}$ alkylbenzene sulfonic acid.

Commercial anionic surfactants which can be used include the sodium salt of dodecylbenzene sulfonic acid sold under the trademark SIPONATE® DS-10 by Alcolac Inc., Baltimore, Md.; sodium n-hexadecyl diphenyloxide disulfonate sold under the trademark DOWFAX® 8390 by The Dow Chemical Company, Midland, Mich.; the sodium salt of a secondary alkane sulfonate sold under the trademark HOSTAPUR® SAS 60 by Clariant Corporation, Charlotte, N.C.; N-acyl taurates such as sodium N-lauroyl methyl taurate sold under the trademark NIKKOL LMT® by Nikko Chemicals Company, Ltd., Tokyo, Japan; and linear alkyl benzene sulfonic acids sold under the trademark BIO-SOFT® S-100 by the Stepan Company, Northfield, Ill. Compositions of the latter type such as dodecylbenzene sulfonic acid, although a catalyst as noted above, can also function as the anionic surfactant when neutralized.

Cationic surfactants useful herein include compounds containing quaternary ammonium hydrophilic moieties in the molecule which are positively charged, such as quaternary ammonium salts represented by $R3R4R5R6N^+X^-$ where R3 to R6 are alkyl groups containing 1-30 carbon atoms, or alkyl groups derived from tallow, coconut oil, or soy; and X is halogen, i.e., chlorine or bromine. Dialkyl dimethyl ammonium salts can be used and are represented by $R7R8N^+(CH_3)_2X^-$ where R7 and R8 are alkyl groups containing 12-30 carbon atoms or alkyl groups derived from tallow, coconut oil, or soy; and X is halogen. Monoalkyl trimethyl ammonium salts can be used and are represented by $R9N^+(CH_3)_3X^-$ where R9 is an alkyl group containing 12-30 carbon atoms or an alkyl group derived from tallow, coconut oil, or soy; and X is halogen.

Representative quaternary ammonium salts are dodecyltrimethyl ammonium chloride/lauryltrimethyl ammonium chloride (LTAC), cetyltrimethyl ammonium chloride (CTAC), didodecyldimethyl ammonium bromide, dihexadecyldimethyl ammonium chloride, dihexadecyldimethyl ammonium bromide, dioctadecyldimethyl ammonium chloride, dieicosyldimethyl ammonium chloride, didocosyldimethyl ammonium chloride, dicoconutdimethyl ammonium chloride, ditallowedimethyl ammonium chloride, and ditallowedimethyl ammonium bromide. These quaternary ammonium salts are commercially available under trademarks such as ADOGEN®, ARQUAD®, TOMAH®, and VARIQUAT®.

Commercially available nonionic surfactants which can be used include compositions such as 2,6,8-trimethyl-4-nonyloxy polyethylene oxyethanols (6EO) and (10EO) sold under the trademarks TERGITOL® TMN-6 and TERGITOL® TMN-10; alkyleneoxy polyethylene oxyethanol ($C_{11-15}$ secondary alcohol ethoxylates 7EO, 9EO, and 15EO) sold under the trademarks TERGITOL® 15-S-7, TERGITOL® 15-S-9, TERGITOL® 15-S-15; other $C_{11-15}$ secondary alcohol ethoxylates sold under the trademarks TERGITOL® 15-S-12, 15-S-20,
15-S-30, 15-S-40; and octylphenoxy polyethoxy ethanol (40EO) sold under the trademark TRITON® X-405. All of these surfactants are sold by Union Carbide Corporation, Danbury, Conn.

Other useful commercial nonionic surfactants are nonylphenoxy polyethoxy ethanol (10EO) sold under the trademark MAKON® 10 by Stepan Company, Northfield, Ill.; polyoxyethylene 23 lauryl ether (Laureth-23) sold commercially under the trademark BRIJ® 35L by ICI Surfactants, Wilmington, Del.; and RENEX® 30, a polyoxyethylene ether alcohol sold by ICI Surfactants, Wilmington, Del.

Protective colloids, i.e., colloidal stabilizers, may be used, if desired, to enhance stability or to provide a specific rheological characteristic to the emulsion. As used herein, the terms protective colloid and/or colloidal stabilizer mean a nonionic molecule that is an effective agent for protecting charged colloidal particles in an aqueous media against flocculation. These compositions typically have a weight average molecular weight between 1,000-300,000 and are typically more hydrophilic than the composition of the first emulsion polymer, as measured by weight-averaged solubility parameters. Colloidal stabilizers which can be used include hydroxyethyl cellulose having a weight average molecular weight between 50,000-150,000; N-vinyl pyrrolidone; polyvinyl alcohol having a weight average molecular weight between 10,000-200,000; partially acetylated polyvinyl alcohol; carboxymethyl cellulose; gums such as gum arabic; starches; proteins; and mixtures thereof. Preferred colloidal stabilizers are hydroxethyl cellulose and polyvinyl alcohol.

Since emulsions are susceptible to microbiological contamination a preservative can be added. Representative preservatives, which can be used include formaldehyde; 1,3-dimethylol-5,5-dimethyl hydantoin, i.e., DMDM Hydantoin; 5-bromo-5-nitro-1,3-dioxane; methyl or propyl paraben; sorbic acid; imidazolidinyl urea; and KATHON® CG (5-chloro-2-methyl-4-isothiazolin-3-one).

Generally, the silicone emulsions contain a siloxane polymer concentration of 10 to 70 percent by weight based on the weight of the total emulsion, preferably 20 to 60 percent by weight. While emulsions containing less than 10 percent siloxane polymer content can be made, such emulsions hold little or no economic value. The surfactant is generally present at 0.05-30 percent by weight based on the weight of the total emulsion, preferably 0.1 to 20 percent by weight. Water and optional ingredients constitute the balance of the emulsion to 100 percent.

Compositions comprising the silicone polyether emulsions may be formulated into personal care products. The personal care compositions of this invention may be in the form of a cream, a gel, a powder, a paste, or a freely pourable liquid. Generally, such compositions can generally be prepared at room temperature if no solid materials at room temperature are presents in the compositions, using simple propeller mixers, Brookfield counter-rotating mixers, or homogenizing mixers. No special equipment or processing conditions are typically required. Depending on the type of form made, the method of preparation will be different, but such methods are well known in the art.

The personal care products may be functional with respect to the portion of the body to which they are applied, cosmetic, therapeutic, or some combination thereof. Conventional examples of such products include, but are not limited to: antiperspirants and deodorants, skin care creams, skin care lotions, moisturizers, facial treatments such as acne or wrinkle removers, personal and facial cleansers, bath oils, perfumes, colognes, sachets, sunscreens, pre-shave and after-shave lotions, shaving soaps, and shaving lathers, hair shampoos, hair conditioners, hair colorants, hair relaxants, hair sprays, mousses, gels, permanents, depilatories, and cuticle coats, make-ups, color cosmetics, foundations, concealers, blushes, lipsticks, eyeliners, mascara, oil removers, color cosmetic removers, and powders, medicament creams, pastes or sprays including antiacne, dental hygienic, antibiotic, healing promotive, nutritive and the like, which may be preventative and/or therapeutic. In general the personal care products may be formulated with a carrier that permits application in any conventional form, including but not limited to liquids, rinses, lotions, creams, pastes, gels, foams, mousses, ointments, sprays, aerosols, soaps, sticks, soft solids, solid gels, and gels. What constitutes a suitable carrier is readily apparent to one of ordinary skill in the art.

The present compositions can be used in a variety of personal, household, and healthcare applications. In particular, the compositions of the present invention may be used in the personal care products as taught in U.S. Pat. Nos. 6,051,216, 5,919,441, 5,981,680; as disclosed in WO 2004/060271 and WO 2004/060101; in sunscreen compositions as taught in WO 2004/060276; in cosmetic compositions also containing film-forming resins, as disclosed in WO 03/105801; in the cosmetic compositions as taught in US Patent Application Publications 2003/0235553, 2003/0072730, 2003/0170188, EP 1,266,647, EP 1,266,648, EP1,266,653, WO 03/105789, WO 2004/000247 and WO 03/106614; as additional agents to those taught in WO 2004/054523; in long wearing cosmetic compositions as taught in US Patent Application Publication 2004/0180032; in transparent or translucent care and/or make up compositions as discussed in WO 2004/054524; all of which are incorporated herein by reference.

The compositions according to this invention can be used by the standard methods, such as applying them to the human body, e.g. skin or hair, using applicators, brushes, applying by hand, pouring them and/or possibly rubbing or massaging the composition onto or into the body. Removal methods, for example for color cosmetics are also well known standard methods, including washing, wiping, peeling and the like. For use on the skin, the compositions according to the present invention may be used in a conventional manner for example for conditioning the skin. An effective amount of the composition for the purpose is applied to the skin. Such effective amounts generally range from about 1 $mg/cm^2$ to about 3 $mg/cm^2$. Application to the skin typically includes working the composition into the skin. This method for applying to the skin comprises the steps of contacting the skin with the composition in an effective amount and then rubbing the composition into the skin. These steps can be repeated as many times as desired to achieve the desired benefit.

The use of the compositions according to the invention on hair may use a conventional manner for conditioning hair. An effective amount of the composition for conditioning hair is applied to the hair. Such effective amounts generally range from about 0.5 g to about 50 g, preferably from about 1 g to about 20 g. Application to the hair typically includes working the composition through the hair such that most or all of the hair is contacted with the composition. This method for conditioning the hair comprises the steps of applying an effective amount of the hair care composition to the hair, and then working the composition through the hair. These steps can be repeated as many times as desired to achieve the desired conditioning benefit.

Non-limiting examples of additives which may be formulated into the personal care compositions in addition to the silicone polyether
emulsions include: additional silicones, anti-oxidants, cleansing agents, colorants, additional conditioning agents, deposition agents, electrolytes, emollients and oils, exfoliating agents, foam boosters, fragrances, humectants, occlusive agents, pediculicides, pH control agents, pigments, preservatives, biocides, other solvents, stabilizers, sun-screening agents, suspending agents, tanning agents, other surfactants, thickeners, vitamins, botanicals, fragrances, waxes, rheology-modifying agents, anti-dandruff, anti-acne, anti-carie and wound healing-promotion agents.

The personal care composition, such as a shampoo or cleanser may contain at least one anionic detersive surfactant. This can be any of the well-known anionic detersive surfactants typically used in shampoo formulations. These anionic detersive surfactants function as cleansing agents and foaming agents in the shampoo compositions of this invention. The anionic detersive surfactants are exemplified by alkali metal sulforicinates, sulfonated glyceryl esters of fatty acids such as sulfonated monoglycerides of coconut oil acids, salts of sulfonated monovalent alcohol esters such as sodium oleylisethianate, amides of amino sulfonic acids such as the sodium salt of oleyl methyl tauride, sulfonated products of fatty acids nitriles such as palmitonitrile sulfonate, sulfonated aromatic hydrocarbons such as sodium alpha-naphthalene monosulfonate, condensation products of naphthalene sulfonic acids with formaldehyde, sodium octahydroanthracene sulfonate, alkali metal alkyl sulfates such as sodium lauryl sulfate, ammonium lauryl sulfate or triethanol amine lauryl sulfate, ether sulfates having alkyl groups of 8 or more carbon atoms such as sodium lauryl ether sulfate, ammonium lauryl ether sulfate, sodium alkyl aryl ether sulfates, and ammonium alkyl aryl ether sulfates, alkylarylsulfonates having 1 or more alkyl groups of 8 or more carbon atoms, alkylbenzenesulfonic acid alkali metal salts exemplified by hexylbenzenesulfonic acid sodium salt, octylbenzenesulfonic acid sodium salt, decylbenzenesulfonic acid sodium salt, dodecylbenzenesulfonic acid sodium salt, cetylbenzenesulfonic acid sodium salt, and myristylbenzenesulfonic acid sodium salt, sulfuric esters of polyoxyethylene alkyl ether including $CH_3(CH_2)_6CH_2O(C_2H_4O)_2SO_3H$, $CH_3(CH_2)_7CH_2O(C_2H_4O)_{3.5}SO_3H$, $CH_3(CH_2)_8CH_2O(C_2H_4O)_8SO_3H$, $CH_3(CH_2)_{19}CH_2O(C_2H_4O)_4SO_3H$, and $CH_3(CH_2)_{10}CH_2O(C_2H_4O)_6SO_3H$, sodium salts, potassium salts, and amine salts of alkylnaphthylsulfonic acid. Preferably the detersive surfactant is selected from the group consisting of sodium lauryl sulfate, ammonium lauryl sulfate, triethanolamine lauryl sulfate, sodium lauryl ether sulfate, and ammonium lauryl ether sulfate. The anionic detersive surfactant is present in the shampoo compositions of this invention in an amount from about 5 to 50 wt % and preferably about 5 to 25 wt % based on the total weight of the composition.

The personal care composition may contain at least one cationic deposition aid, preferably a cationic deposition polymer. The cationic deposition aid will generally be present at levels of from 0.001 to 5%, preferably from about 0.01 to 1%, more preferably from about 0.02% to about 0.5% by weight.

The polymer may be a homopolymer or be formed from two or more types of monomers. The molecular weight of the polymer will generally be between 5 000 and 10 000 000, typically at least 10 000 and preferably in the range 100 000 to about 2 000 000. The polymers will have cationic nitrogen containing groups such as quaternary ammonium or protonated amino groups, or a mixture thereof. The cationic charge density has been found to need to be at least 0.1 meq/g, preferably above 0.8 or higher. The cationic charge density should not exceed 4 meq/g, it is preferably less than 3 and more preferably less than 2 meq/g. The charge density can be measured using the Kjeldahl method and should be within the above limits at the desired pH of use, which will in general be from about 3 to 9 and preferably between 4 and 8. The cationic nitrogen-containing group will generally be present as a substituent on a fraction of the total monomer units of the cationic deposition polymer. Thus when the polymer is not a homopolymer it can contain spacer noncationic monomer units. Such polymers are described in the CTFA Cosmetic Ingredient Directory, 3rd edition. Suitable cationic deposition aids include, for example, copolymers of vinyl monomers having cationic amine or quaternary ammonium functionalities with water soluble spacer monomers such as (meth) acrylamide, alkyl and dialkyl (meth)acrylamides, alkyl (meth)acrylate, vinyl caprolactone and vinyl pyrrolidine. The alkyl and dialkyl substituted monomers preferably have C1-C7 alkyl groups, more preferably C1-3 alkyl groups. Other suitable spacers include vinyl esters, vinyl alcohol, maleic anhydride, propylene glycol and ethylene glycol. The cationic amines can be primary, secondary or tertiary amines, depending upon the particular species and the pH of the composition. In general secondary and tertiary amines, especially tertiary, are preferred. Amine substituted vinyl monomers and amines can be polymerized in the amine form and then converted to ammonium by quaternization. Suitable cationic amino and quaternary ammonium monomers include, for example, vinyl compounds substituted with dialkyl aminoalkyl acrylate, dialkylamino alkylmethacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidine, e.g., alkyl vinyl imidazolium, and quaternized pyrrolidine, e.g., alkyl vinyl imidazolium, alkyl vinyl pyridinium, alkyl vinyl pyrrolidine salts. The alkyl portions of these monomers are preferably lower alkyls such as the $C_1$-$C_3$ alkyls, more preferably C, and C2 alkyls. Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide. The cationic deposition aids can comprise mixtures of monomer units derived from amine- and/or quaternary ammonium-substituted monomer and/or compatible spacer monomers. Suitable cationic deposition aids include, for example: copolymers of 1-vinyl-2-pyrrolidine and 1-vinyl-3-methylimidazolium salt (e.g., Chloride salt) (referred to in the industry by the Cosmetic, Toiletry, and Fragrance Association, "CTFA". as Polyquaternium-16) such as those commercially available from BASF Wyandotte Corp. (Parsippany, N.J., USA) under the LUVIQUAT tradename (e.g., LUVIQUAT FC 370); copolymers of 1-vinyl-2-pyrrolidine and dimethylaminoethyl methacrylate (referred to in the industry by CTFA as Polyquaternium-11) such as those commercially from Gar Corporation (Wayne, N.J., USA) under the GAFQUAT tradename (e.g., GAFQUAT 755N); cationic diallyl quaternary ammonium-containing polymer including, for example, dimethyldiallyammonium chloride homopolymer and copolymers of acrylamide and dimethyldiallyammonium chloride, referred to in the industry (CTFA) as Polyquaternium 6 and Polyquaternium 7, respectively; mineral acid salts of aminoalkyl esters of homo- and co-polymers of unsaturated carboxylic acids having from 3 to 5 carbon atoms, as described in U.S. Pat. No. 4,009,256; and cationic polyacrylamides as described in our copending UK Application No. 9403156.4 (W095/22311). Other cationic deposition aids that can be used include polysaccharide polymers, such as cationic cellulose derivatives and cationic starch derivatives. Cationic polysaccharide polymer materials suitable for use in compositions of the invention include those of the formula: A-O(R—N$^+$R$^1$R$^2$R$^3$X$^-$) wherein: A is an anhydroglucose residual group, such as starch or cellulose anhydroglucose residual, R is an alkylene oxyalklene, polyoxyalkylene, or hydroxyalkylene group, or combination thereof, R', R~' and R3 independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in R', R 2 and R') preferably being about 20 or less, and X is an anionic counterion, as previously described. Cationic cellulose is available from Amerchol Corp. (Edison, N.J., USA) in their Polymer iR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200. Other cationic deposition aids that can be used include cationic guar gum derivatives, such as guar hydroxypropyltrimonium chloride (Commercially available from Celanese Corp. in their Jaguar trademark series). Other materials include quaternary nitrogen-containing cellulose ethers (e.g., as described in U.S. Pat. No. 3,962,418, incorporated by reference herein), and copolymers of etherified cellulose and starch (e.g., as described in U.S. Pat. No. 3,958,581, incorporated by reference herein).

The personal care composition may contain a foam boosting agent. A foam booster is an agent which increases the amount of foam available from a system at a constant molar concentration of surfactant, in contrast to a foam stabilizer which delays the collapse of a foam. Foam building is provided by adding to the aqueous media an effective amount of a foam boosting agent. The foam boosting agent is preferably selected from the group consisting of fatty acid alkanolamides and amine oxides. The fatty acid alkanolamides are exemplified by isostearic acid diethanolamide, lauric acid diethanolamide, capric acid diethanolamide, coconut fatty acid diethanolamide, linoleic acid diethanolamide, myristic acid diethanolamide, oleic acid diethanolamide, stearic acid diethanolamide, coconut fatty acid monoethanolamide, oleic acid monoisopropanolamide, and lauric acid monoisopropanolamide. The amine oxides are exemplified by N-cocodimethylamine oxide, N-lauryl dimethylamine oxide, N-myristyl dimethylamine oxide, N-stearyl dimethylamine oxide, N-cocamidopropyl dimethylamine oxide, N-tallowamidopropyl dimethylamine oxide, bis(2-hydroxyethyl) C12-15 alkoxypropylamine oxide. Preferably a foam booster is selected from the group consisting of lauric acid diethanolamide, N-lauryl dimethylamine oxide, coconut acid diethanolamide, myristic acid diethanolamide, and oleic acid diethanolamide. The foam boosting agent is preferably present in the shampoo compositions of this invention in an amount from about 1 to 15 wt % and more preferably about 2 to 10 wt % based on the total weight of the composition. The composition may further comprise a polyalkylene glycol to improve lather performance. Concentration of the polyalkylene glycol in the shampoo composition may range from about 0.01% to about 5%, preferably from about 0.05% to about 3%, and more preferably from about 0.1% to about 2%, by weight of the composition. The optional polyalkylene glycols are characterized by the general formula: H(OCH2CHR)n-OH wherein R is selected from the group consisting of H, methyl, and mixtures thereof. When R is H, these materials are polymers of ethylene oxide, which are also known as polyethylene oxides, polyoxyethylenes, and polyethylene glycols. When R is methyl, these materials are polymers of propylene oxide, which are also known as polypropylene oxides, polyoxypropylenes, and polypropylene glycols. When R is methyl, it is also understood that various positional isomers of the resulting polymers can exist. In the above structure, n has an average value of from about 1500 to about 25,000, preferably from about 2500 to about 20,000, and more preferably from about 3500 to about 15,000. Polyethylene glycol polymers useful herein are PEG-2M wherein R equals H and n has an average value of about 2,000 (PEG-2M is also known as Polyox WSR9 N-10, which is available from Union Carbide and as PEG-2,000); PEG-5M wherein R equals H and n has an average value of about 5,000 (PEG-5M is also known as Polyox WSRO N-35 and Polyox WSRS N-80, both available from Union Carbide and as PEG-5,000 and Polyethylene Glycol 300,000); PEG-7M wherein R equals H and n has an average value of about 7,000 (PEG-7M is also known as Polyox WSRO N-750 available from Union Carbide); PEG-9M wherein R equals H and n has an average value of about 9,000 (PEG 9-M is also known as Polyox WSRS N-3333 available from Union Carbide); and PEG14 M wherein R equals H and n has an average value of about 14,000 (PEG-14M is also known as Polyox WSRO N-3000 available from Union Carbide). Other useful polymers include the polypropylene glycols and mixed polyethylene/polypropylene glycols.

The personal care composition may contain a suspending agent at concentrations effective for suspending the preferred silicone conditioning agent, or other water-insoluble material, in dispersed form in the shampoo compositions. Such concentrations range from about 0.1% to about 10%, preferably from about 0.3% to about 5.0%, by weight of the shampoo compositions. Suspending agents include crystalline suspending agents which can be categorized as acyl derivatives, long chain amine oxides, and mixtures thereof, concentrations of which range from about 0.1% to about 5.0%, preferably from about 0.5% to about 3.0%, by weight of the shampoo compositions. These suspending agents are described in U.S. Pat. No. 4,741,855, which description is incorporated herein by reference. These preferred suspending agents include ethylene glycol esters of fatty acids preferably having from about 16 to about 22 carbon atoms. More preferred are the ethylene glycol stearates, both mono and distearate, but particularly the distearate containing less than about 7% of the mono stearate. Other suitable suspending agents include alkanol amides of fatty acids, preferably having from about 16 to about 22 carbon atoms, more preferably about 16 to 18 carbon atoms, preferred examples of which include stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); glyceryl esters (e.g., glyceryl distearate) and long chain esters of long chain alkanol amides (e.g., stearamide diethanolamide distearate, stearamide monoethanolamide stearate). Long chain acyl derivatives, ethylene glycol esters of long chain carboxylic acids, long chain amine oxides, and alkanol amides of long chain carboxylic acids in addition to the preferred materials listed above may be used as suspending agents. For example, it is contemplated that suspending agents with long chain hydrocarbyls having C8-C22 chains may be used. Other long chain acyl derivatives suitable for use as suspending agents include N,N-dihydrocarbyl amido benzoic acid and soluble salts thereof (e.g., Na, K), particularly N,N-di(hydrogenated) C16, C18 and tallow amido benzoic acid species of this family, which are commercially available from Stepan Company (Northfield, Ill., USA). Examples of suitable long chain amine oxides for use as suspending agents include alkyl (C16-C22) dimethyl amine oxides, e.g., stearyl dimethyl amine oxide. Other suitable suspending agents include xanthan gum at concentrations ranging from about 0.3% to about 3%, preferably from about 0.4% to about 1.2%, by weight of the shampoo compositions. The use of xanthan gum as a suspending agent in silicone containing shampoo compositions is described, for example, in U.S. Pat. No. 4,788,006, which description is incorporated herein by reference. Combinations of long chain acyl derivatives and xanthan gum may also be used as a suspending agent in the shampoo compositions. Such combinations are described in U.S. Pat. No. 4,704,272, which description is incorporated herein by reference. Other suitable suspending agents include carboxyvinyl polymers. Preferred among these polymers are the copolymers of acrylic acid crosslinked with polyallylsucrose as described in U.S. Pat. No. 2,798,053, which description is incorporated herein by reference. Examples of these polymers include Carbopol 934, 940, 941, and 956. available from B. F. Goodrich Company. Other suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow)amine. Still other suitable suspending agents include di(hydrogenated tallow) phthalic acid amide, and crosslinked maleic anhydridemethyl vinyl ether copolymer. Other suitable suspending agents may be used in the shampoo compositions, including those that can impart a gel-like viscosity to the composition, such as water soluble or colloidally water soluble polymers like cellulose ethers (e.g., methylcellulose, hydroxybutyl methylcellulose, hyroxypropylcellulose, hydroxypropyl methylcellulose, hydroxyethyl ethylcellulose and hydroxyethylcellulose), guar gum, polyvinyl alcohol, polyvinyl pyrrolidone, hydroxypropyl guar gum, starch and starch derivatives, and other thickeners, viscosity modifiers, gelling agents, etc.

The personal care composition may contain one or more water-soluble emollients including, but not limited to, lower molecular weight aliphatic diols such as propylene glycol and butylene glycol; polyols such as glycerine and sorbitol; and polyoxyethylene polymers such as polyethylene glycol 200. The specific type and amount of water soluble emollient(s) employed will vary depending on the desired aesthetic characteristics of the composition, and is readily determined by one skilled in the art.

The personal care composition may contain various oils. The term "oil" as used herein refers to any material which is substantially insoluble in water. When the composition is to be used in a cosmetic or personal care product, the product components must also be cosmetically acceptable or otherwise meet the conditions of the end use product. Suitable oil components include, but are not limited to, natural oils such as coconut oil; hydrocarbons such as mineral oil and hydrogenated polyisobutene; fatty alcohols such as octyldodecanol; esters such as C12-C15 alkyl benzoate; diesters such as propylene dipelarganate; and triesters, such as glyceryl trioctanoate and silicones especially cyclomethicone and dimethicone and mixtures thereof. The composition of the invention also contains oils, preferably a mixture of low viscosity and high viscosity oils. Suitable low viscosity oils have a viscosity of 5 to 100 mPa·s at 25° C., and are generally esters having the structure RCO—OR' wherein RCO represents the carboxylic acid radical and wherein OR' is an alcohol residue. Examples of these low viscosity oils include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, cocodicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or mixtures of octyldodecanol, acetylated lanolin alcohol, cetyl acetate, isododecanol, polyglyceryl-3-diisostearate, or mixtures thereof. The high viscosity surface oils generally have a viscosity of 200-1,000,000 mPa·s at 25° C., preferably a viscosity of 100,000-250,000 mPa·s. Surface oils include castor oil, lanolin and lanolin derivatives, triisocetyl citrate, sorbitan sesquioleate, C10-18 triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or mixtures thereof. The suggested ratio of low viscosity to high viscosity oils in the oil phase is 1:15 to 15:1, preferably 1:10 to 10:1 respectively. The preferred formulation of the invention comprises 1 to 20% of a mixture of low viscosity and high viscosity surface oils. Mention may be made, among the optional other non-silicone fatty substances, of mineral oils, such as liquid paraffin or liquid petroleum, of animal oils, such as perhydrosqualene or arara oil, or alternatively of vegetable oils, such as sweet almond, calophyllum, palm, castor, avocado, jojoba, olive or cereal germ oil. It is also possible to use esters of lanolic acid, of oleic acid, of lauric acid, of stearic acid or of myristic acid, for example; alcohols, such as oleyl alcohol, linoleyl or linolenyl alcohol, isostearyl alcohol or octyldodecanol; or acetylglycerides, octanoates, decanoates or ricinoleates of alcohols or of polyalcohols. It is alternatively possible to use hydrogenated oils which are solid at 25° C., such as hydrogenated castor, palm or coconut oils, or hydrogenated tallow; mono-, di-, trior sucroglycerides; lanolins; or fatty esters which are solid at 25° C.

The personal care composition may contain various waxes. The waxes or wax-like materials generally have a melting point range of 35 to 120° C. at atmospheric pressure. Waxes in this category include synthetic wax, ceresin, paraffin, ozokerite, illipe butter, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, or mixtures thereof. The preferred formulation of the invention comprises about 10-30% of a mixture of waxes. Mention may be made, among the waxes capable of being used as non-silicone fatty substances, of animal waxes, such as beeswax; vegetable waxes, such as carnauba, candelilla, ouricury or japan wax or cork fibre or sugarcane waxes; mineral waxes, for example paraffin or lignite wax or microcrystalline waxes or ozokerites; synthetic waxes, including polyethylene waxes, and waxes obtained by the Fischer-Tropsch synthesis. Mention may be made, among the silicone waxes, of polymethylsiloxane alkyls, alkoxys and/or esters.

Thickening agent may be added to provide a convenient viscosity. For example, viscosities within the range of 500 to 25,000 mm$^2$/s at 25° C. or more alternatively in the range of 3,000 to 7,000 mm$^2$/s are usually suitable. Suitable thickening agents are exemplified by sodium alginate, gum arabic, polyoxyethylene, guar gum, hydroxypropyl guar gum, ethoxylated alcohols, such as laureth-4 or polyethylene glycol 400, cellulose derivatives exemplified by methylcellulose, methylhydroxypropylcellulose, hydroxypropylcellulose, polypropylhydroxyethylcellulose, starch, and starch derivatives exemplified by hydroxyethylamylose and starch amylose, locust bean gum, electrolytes exemplified by sodium chloride and ammonium chloride, and saccharides such as fructose and glucose, and derivatives of saccharides such as PEG-120 methyl glucose diolate or mixtures of 2 or more of these. Alternatively the thickening agent is selected from cellulose derivatives, saccharide derivatives, and electrolytes, or from a combination of two or more of the above thickening agents exemplified by a combination of a cellulose derivative and any electrolyte, and a starch derivative and any electrolyte. The thickening agent, where used is present in the shampoo compositions of this invention in an amount sufficient to provide a viscosity in the final shampoo composition of from 500 to 25,000 mm$^2$/s. Alternatively the thickening agent is present in an amount from about 0.05 to 10 wt % and alternatively 0.05 to 5 wt % based on the total weight of the composition.

Stabilizing agents can be used in the water phase of the compositions. Suitable water phase stabilizing agents can include alone or in combination one or more electrolytes, polyols, alcohols such as ethyl alcohol, and hydrocolloids. Typical electrolytes are alkali metal salts and alkaline earth salts, especially the chloride, borate, citrate, and sulfate salts of sodium, potassium, calcium and magnesium, as well as aluminum chlorohydrate, and polyelectrolytes, especially hyaluronic acid and sodium hyaluronate. When the stabilizing agent is, or includes, an electrolyte, it amounts to about 0.1 to 5 wt % and more alternatively 0.5 to 3 wt % of the total composition. The hydrocolloids include gums, such as Xantham gum or Veegum and thickening agents, such as carboxymethyl cellulose. Polyols, such as glycerine, glycols, and sorbitols can also be used. Alternative polyols are glycerine, propylene glycol, sorbitol and butylene glycol. If a large amount of a polyol is used, one need not add the electrolyte. However, it is typical to use a combination of an electrolyte, a polyol and an hydrocolloid to stabilize the water phase, e.g. magnesium sulfate, butylene glycol and Xantham gum.

The composition according to the invention can also be under the form of aerosols in combination with propellant gases, such as carbon dioxide, nitrogen, nitrous oxide, volatile hydrocarbons such as butane, isobutane, or propane and chlorinated or fluorinated hydrocarbons such as dichlorodifluoromethane and dichlorotetrafluoroethane or dimethylether.

Silicone compositions other than the silicone amino polyether block copolymer emulsions, may also be included in the personal care compositions. For example, such silicones include; silicone fluids, gums, resins, elastomers; silicone surfactants and emulsifiers such as silicone polyethers, organofunctional silicones such as aminofunctional silicones and alkylmethylsiloxanes.

Alkylmethylsiloxanes may be included in the present compositions. These siloxane polymers generally will have the formula Me$_3$SiO[Me$_2$SiO]$_y$[MeRSiO]$_z$SiMe$_3$, in which R is a hydrocarbon group containing 6-30 carbon atoms, Me represents methyl, and the degree of polymerization (DP), i.e., the sum of y and z is 3-50. Both the volatile and liquid species of alkymethylsiloxanes can be used in the composition.

Silicone gums may be included in the present compositions. Polydiorganosiloxane gums are known in the art and are available commercially. They consist of generally insoluble polydiorganosiloxanes having a viscosity in excess of 1,000,000 centistoke (mm$^2$/s) at 25° C., alternatively greater than 5,000,000 centistoke (mm$^2$/s) at 25° C. These silicone gums are typically sold as compositions already dispersed in a suitable solvent to facilitate their handling. Ultra-high viscosity silicones can also be included as optional ingredients. These ultra-high viscosity silicones typically have a kinematic viscosity greater than 5 million centistoke (mm$^2$/s) at 25° C., to about 20 million centistoke (mm$^2$/s) at 25° C. Compositions of this type in the form of suspensions are most preferred, and are described for example in U.S. Pat. No. 6,013,682 (Jan. 11, 2000).

Silicone resins may be included in the present compositions. These resin compositions are generally highly crosslinked polymeric siloxanes. Crosslinking is obtained by incorporating trifunctional and/or tetrafunctional silanes with the monofunctional silane and/or difunctional silane monomers used during manufacture. The degree of crosslinking required to obtain a suitable silicone resin will vary according to the specifics of the silane monomer units incorporated during manufacture of the silicone resin. In general, any silicone having a sufficient level of trifunctional and tetrafunctional siloxane monomer units, and hence possessing sufficient levels of crosslinking to dry down to a rigid or a hard film can be considered to be suitable for use as the silicone resin. Commercially available silicone resins suitable for applications herein are generally supplied in an unhardened form in low viscosity volatile or nonvolatile silicone fluids. The silicone resins should be incorporated into compositions of the invention in their non-hardened forms rather than as hardened resinous structures.

Silicone carbinol fluids may be included in the present compositions. These materials are described in WO 03/101412 A2, and can be commonly described as substituted hydrocarbyl functional siloxane fluids or resins.

Water soluble or water dispersible silicone polyether compositions may be included in the present compositions: These are also known as polyalkylene oxide silicone copolymers, silicone poly(oxyalkylene) copolymers, silicone glycol copolymers, or silicone surfactants. These can be linear rake or graft type materials, or ABA type where the B is the siloxane polymer block, and the A is the poly(oxyalkylene) group. The poly(oxyalkylene) group can consist of polyethylene oxide, polypropylene oxide, or mixed polyethylene oxide/polypropylene oxide groups. Other oxides, such as butylene oxide or phenylene oxide are also possible.

Compositions according to the invention can be used in w/o, w/s, or multiple phase emulsions using silicone emulsifiers. Typically the water-in-silicone emulsifier in such formulation is non-ionic and is selected from polyoxyalkylene-substituted silicones, silicone alkanolamides, silicone esters and silicone glycosides. Suitable silicone-based surfactants are well known in the art, and have been described for example in U.S. Pat. No. 4,122,029 (Gee et al.), U.S. Pat. No. 5,387,417 (Rentsch), and U.S. Pat. No. 5,811,487 (Schulz et al).

EXAMPLES

These examples are intended to illustrate the invention to one of ordinary skill in the art and should not be interpreted as limiting the scope of the invention set forth in the claims. All measurements and experiments were conducted at 23° C., unless indicated otherwise.

Example 1

Synthesis of an Epoxy Terminal (Ab)n Silicone Polyether Copolymer

To a 1 L flask was added 408.18 g of a 35 DP Si—H terminal polydimethylsiloxane, 0.4825 g of SYL-OFF 4000 (0.52 wt % Pt), and 58.16 g of 2-propanol. The headspace was purged with $N_2$ and the reactants were heated to 70° C. 79.82 g of NOF Uniox DMUS-5 [dimethallyl terminal poly(ethylene oxide)] was added dropwise. Upon observation of a mild exotherm (~2° C.), the temperature was increased to 90° C. during the addition of the polyether. Upon complete addition of the poly(ethylene oxide) (~20 minutes), the reaction mixture was allowed to heat for 1 hour. To this, 13.04 g of allyl glycidyl ether was added dropwise. The reaction was heated an additional 3 hours at 90° C. Upon completion, the volatiles were removed in vacuo. Analysis of the polymer by $^{29}Si$ NMR suggests a value of n equal to 2.4 resulting in a calculated molecular weight of 11,300 g/mol corresponding to an average structure of: $CH_2(O)CHCH_2OCH_2CH_2CH_2[SiMe_2(OSiMe_2)_{35}OSiMe_2 CH_2CH(CH_3)CH_2O(CH_2CH_2O)_{14}CH_2CH(CH_3)CH_2]_{2.4} SiMe_2O(SiMe_2O)_{35}OSiMe_2CH_2CH_2CH_2OCH_2CH(O)CH_2$.
Synthesis of an Amine Terminal (AB)n Silicone Polyether Copolymer:

To a 250 mL flask was added 100.03 g of the above epoxy terminal (AB)n silicone polyether copolymer, 2.94 g of diisopropanolamine, and 24.87 g of 2-propanol. The headspace was purged with $N_2$ and the mixture was heated at reflux for 4 hours. Volatiles were removed in vacuo. Analysis by $^{13}C$ NMR confirms disappearance of the epoxy moiety due to reaction with the amine. In terms of composition based on the functional portions, the polymer is 81 wt % silicone, 13 wt % ethylene oxide, and 0.49 wt % nitrogen.

Example 2

Preparation of Emulsion A

The emulsification procedure was on performed on a Hauschild Speedmixer (Model DAC 150 FVZ). To a plastic 20 g size cup was added 10.18 g of the silicone copolymer from Example 1 along with 0.53 g of Brig 35L surfactant and 3.12 g of water. The mixture was sheared at maximum speed for 20 seconds. The gel-like phase and particles were worked with a spatula to aid incorporation of the water phase. The shear step and subsequent working with the spatula were repeated until all of the water was incorporated to create a homogeneous mixture. A final addition of 3.00 g of water was made and the emulsion of was again mixed on the Speedmixer.

Example 3

Preparation of Emulsion B

To a 20 g cup was added 4.1 g of the silicone copolymer described in Example 1. To the vessel, 0.099 g of lactic acid, 4.0 g of Brij 35L, and 2.2 g of water was added. The mixture was sheared for 20 seconds at maximum speed on the Speedmixer. Aliquots of 1-3 g of water were added until a total of 10.1 g had been added. The mixture was sheared on the Speedmixer after each addition and worked with a spatula to aid incorporation of the water into the gel-like phase.

Example 4

Preparation of Emulsion C

To a plastic 20 g size cup was added 10.20 g of an (AB)n silicone polyether copolymer synthesized in an analogous manner as Example 1 (MW=25,300; 91 wt % silicone, 5.8 wt % ethylene oxide, 0.22 wt % nitrogen extrapolated from analysis by NMR). To the cup was also added 0.60 g of Brig 35L surfactant and 2.30 g of water. The mixture was sheared at maximum speed for 20 seconds. The gel-like phase and particles were worked with a spatula to aid incorporation of the water phase. The shear step and subsequent working with the spatula were repeated until all of the water was incorporated to create a homogeneous mixture. Further additions of 1.3, 2.1, and 0.80 g of water were made with shearing in the Speedmixer.

Example 5

Preparation of Emulsion D

To a 20 g Speedmixer cup was added 4.2 g of the (AB)n silicone polyether copolymer described in Example 4. To the vessel was also added 0.063 g of lactic acid, 4.2 g of Brij 35L, and 2.3 g of water. The mixture was sheared for 20 seconds at maximum speed on the Speedmixer. Aliquots of 1-3 g of water were added until a total of 9.5 g had been added. The mixture was sheared on the Speedmixer after each addition and worked with a spatula to aid incorporation of the water into the gel-like phase.

Example 6

Preparation of Emulsion E

To a 100 g Speedmixer cup was added 20.0 g of the (AB)n silicone polyether copolymer (MW=30,100; 87 wt % silicone, 11 wt % ethylene oxide, 0.19 wt % nitrogen extrapolated from analysis by NMR). To the vessel was also added 0.963 g of lactic acid, 20.8 g of Brij 35L, and 9.1 g of water. The mixture was sheared for 30 seconds at maximum speed on the Speedmixer. Aliquots of 8-12 g of water were added until a total of 50.4 g had been added. The mixture was sheared on the Speedmixer after each addition and worked with a spatula to aid incorporation of the water into the gel-like phase.

Example 7

Preparation of Emulsion F

To a 100 g Speedmixer cup was added 20.2 g of the (AB)n silicone polyether copolymer (MW=38,400; 93 wt % silicone, 4.9 wt % ethylene oxide, 0.15 wt % nitrogen extrapolated from analysis by NMR). To the vessel was also added 0.128 g of lactic acid, 20.2 g of Brij 35L, and 9.5 g of water. The mixture was sheared for 30 seconds at maximum speed on the Speedmixer. Aliquots of 7-12 g of water were added until a total of 49.6 g had been added. The mixture was sheared on the Speedmixer after each addition and worked with a spatula to aid incorporation of the water into the gel-like phase.

Example 8

Preparation of Emulsion G

To a 250 mL stainless steel beaker was added 20.19 g of the silicone polyether copolymer described in Example 7 along with 6.67 g of Tergitol 15-S-12 and 3.34 g of Tergitol 15-S-5. The components were mixed at 500 rpm for five minutes using a Cowles blade affixed to a Caframo mixer (type RZR50). After addition of 0.5 mL of acetic acid, mixing was resumed for an additional 5 minutes. During mixing, 10.10 g of DI water was added slowly and shearing was allowed to continue for 10 minutes. An additional aliquot of DI water, 10.24 g, was added and mixing continued for 30 minutes. Another portion of DI water, 10.19 g was added and followed by continued mixing over 30 minutes. The mixer was stopped occasionally and the walls were scraped down to ensure full incorporation of the polymer into the water phase. A final addition of 29.57 g of DI water was made and the emulsion was mixed for 3 hours. After collecting the emulsion, 9.90 g of DI water were added to adjust the actives content to the desired level.

Example 9

Synthesis of a Chain-Extended Amino Functional (AB)n Silicone Polyether Copolymer To a 2 L flask was added 131.7 g of NOF DMUS-5 [dimethallyl terminal poly(ethylene oxide)], 1.76 g of a Pt solution (0.33 wt % Pt in IPA, diluted Dow Corning 2-0719 catalyst), and 111.2 g of ethylacetate. The headspace was purged with $N_2$ and the reactants were heated to 70° C. To the flask was added 868.5 g of a 42 DP Si—H terminal polydimethylsiloxane dropwise over 30 minutes. Upon observation of a mild exotherm (~2° C.) change in color of the reaction mixture to light yellow, the temperature was increased to 90° C. during the addition of the siloxane polymer. Upon complete addition of the siloxane polymer, the reaction mixture was allowed to heat for 2 hours wherein 24.31 g of allyl glycidyl ether was then added. The reaction was allowed to heat for 4 hours at 100° C. Upon completion, the volatiles were removed in vacuo. Analysis of the polymer by $^{29}Si$ NMR suggests a value of n equal to 1.5 resulting in a calculated molecular weight of 9,600 g/mol corresponding to an average structure of:
$CH_2(O)CHCH_2OCH_2CH_2CH_2[SiMe_2(OSiMe_2)_{42}OSiMe_2$
$CH_2CH(CH_3)CH_2O(CH_2CH_2O)_{14}CH \quad 2CH(CH_3)CH_2]_{1.5}$
$SiMe_2O(SiMe_2O)_{42}OSiMe_2CH_2CH_2CH_2OCH_2CH(O)CH_2$.
To a 1 L flask was added 444.7 g of the epoxy terminal (AB)n silicone copolymer, 5.38 g of piperazine, and 151.1 g of 2-propanol. The contents were heated at reflux for 12 hours. The volatile components were then removed in vacuo. Analysis by $^{13}C$ and $^{29}Si$ NMR spectroscopy suggests a molecular weight of 23,400 g/mol was obtained with a composition of the amino functional chain-extended polymer of 82 wt % silicone, 9.3 wt % ethylene oxide, and 0.41 wt % nitrogen.

Example 10

Preparation of Emulsion H

To a 100 g Speedmixer cup was added 59.99 g of the chain-extended amino functional (AB)n silicone polyether copolymer described in Example 9. To the vessel was also added 0.21 g of lactic acid, 3.38 g of Brij 35L, and 15.1 g of DI water. The mixture was sheared for 30 seconds at maximum speed on the Speedmixer. Aliquots of 5-7 g of water were added until a total of 22.04 g had been added. The mixture was sheared on the Speedmixer after each addition and worked with a spatula to aid incorporation of the water into the gel-like phase.

Example 11

Preparation of Emulsion I

To a 100 g Speedmixer cup was added 60.00 g of an alternative chain-extended amino functional (AB)n silicone polyether copolymer (MW=23,900; 92 wt % silicone, 3.5 wt % ethylene oxide, 0.26 wt % nitrogen extrapolated from analysis by NMR) synthesized in an analogous manner to Example 9. To the vessel was also added 0.13 g of lactic acid, 3.88 g of Brij 35L, and 15.1 g of DI water. The mixture was sheared for 30 seconds at maximum speed on the Speedmixer. Aliquots of 5-11 g of water were added until a total of 22.1 g had been added. The mixture was sheared on the Speedmixer after each addition and worked with a spatula to aid incorporation of the water into the gel-like phase.

TABLE 1

Emulsion Compositions

| Emulsion ID | Example # | % Silicone Polymer | $D_{50}$ Particle Size (μm) |
| --- | --- | --- | --- |
| A | 2 | 60.5 | 0.69 |
| B | 3 | 20.1 | 0.16 |
| C | 4 | 59.0 | 2.39 |
| D | 5 | 20.8 | 0.22 |
| E | 6 | 19.7 | 1.57 |
| F | 7 | 20.3 | 0.23 |
| G | 8 | 20.1 | 0.04 |
| H | 10 | 59.6 | 0.54 |
| I | 11 | 59.3 | 1.56 |

Example 12

Hair Conditioner Formulations

Samples of silicone amino polyether block copolymer emulsions were added to rinse-off conditioning formulations using two percent by weight of the silicone. The conditioning formulations are shown in Table 2. The conditioners of the present invention were prepared using Emulsions A, B, C and D from Table 1. A conditioner containing a commercial non-ionic amino siloxane microemulsion, cationic amino siloxane emulsion, and comparative silicone amino SPE ABn copolymer emulsion were also tested for comparison purposes.

TABLE 2

| | Conditioners | | | | | | |
|---|---|---|---|---|---|---|---|
| Ingredient | Weight Percent | Weight Percent | Weight Percent | Weight Percent | Weight Percent | Weight Percent | Weight Percent |
| Deionized Water | q.s. to 100% | q.s. to 100% | q.s. to 100% | q.s. to 100% | q.s. to 100% | q.s. to 100% | q.s. to 100% |
| Hydroxyethyl-cellulose[1] | 1.5 | 1.5 | 1.5 | 1.5 | 1.5 | 1.5 | 1.5 |
| Cetearyl Alcohol[2] | 1.0 | 1.0 | 1.0 | 1.0 | 1.0 | 1.0 | 1.0 |
| PEG-100 Stearate & Glyceryl Stearate[3] | 1.0 | 1.0 | 1.0 | 1.0 | 1.0 | 1.0 | 1.0 |
| A Emulsion[4] | 3.3 | — | — | — | — | — | — |
| B Emulsion[5] | — | 10.0 | — | — | — | — | — |
| C Emulsion[6] | — | — | 3.4 | — | — | — | — |
| D Emulsion[7] | — | — | — | 9.6 | — | — | — |
| Amino Siloxane Microemulsion[8] | — | — | — | — | 10.0 | — | — |
| Amino Siloxane Emulsion[9] | — | — | — | — | — | 5.7 | — |
| Comparative Silicone Amino Polyether Block Copolymer Emulsion[10] | — | — | — | — | — | — | 9.3 |
| DMDM Hydantoin[11] | 0.2 | 0.2 | 0.2 | 0.2 | 0.2 | 0.2 | 0.2 |

[1] Natrosol ® 250 HHR available from Hercules of Wilmington, DE
[2] Crodocol CS-50 ® available from Croda Inc. of Edison, NJ
[3] Arlacel ® 165 available from Uniqema of Wilmington, DE
[4] A, concentration based on 2% active silicone level, (60.5% Active)
[5] B, concentration based on 2% active silicone level, (20.1% Active)
[6] C, concentration based on 2% active silicone level, (59.0% Active)
[7] D, concentration based on 2% active silicone level, (20.8% Active)
[8] Dow Corning ® CE-8170 AF Microemulsion available from Dow Corning, Midland, MI, concentration based on 2% active silicone level (20% active)
[9] Dow Corning ® 949 Emulsion available from Dow Corning, Midland, MI, concentration based on 2% active silicone level (35% active)
[10] Dow Corning ® CE 8401 Emulsion available from Dow Corning, Midland, MI, concentration based on 2% active silicone level (21.5% active)
[11] Glydant ® available from Lonza, Inc. of Fairlawn, NJ Deionized water is added to the mixing vessel and heated to 75° C. With moderate agitation, the hydroxyethyl cellulose is dispersed until fully dissolved. Heat is decreased to 60° C. and cetearyl alcohol and PEG-100 stearate and glyceryl stearate is added. Heat is then decreased to 40° and the silicone silicone amino polyether block copolymer emulsion is added to the base conditioner. The conditioner is mixed for 5-10 minutes and then DMDM hydantoin is added. The water loss is compensated for and the formulation is mixed for an additional 5 minutes. The final pH of the conditioner formulations are all approximately 6-7.

Procedure—Preparation of Hair Sample

Slightly bleached European human hair from International Hair Importer and Products, Inc. was used for testing the conditioners prepared herein. A master hand of hair about eight inches in length was subdivided into a series of individual hair tresses. Each tress weighed about 2.5 grams. A 0.5 inch (1.27 cm) of the root end of the hair was trimmed and glued to a 2 inch by 2 inch (5.08 cm by 5.08 cm) plastic tab using DUCO CEMENT®. The cement was allowed to dry, and the hair tress was combed and trimmed to a length such that six inches (15.24 cm) of hair extended below the bottom of the plastic tab. A hole was punched in middle of tab about one fourth inch (0.635 cm) from its top. Each tress was rinsed for 15 seconds under a stream of 40° C. tap water. Using a pipette, 1.0 gram of a solution containing nine percent of sodium lauryl sulfate was applied and lathered through the tress for 30 seconds. The tress was rinsed for 30 seconds under running water. Excess water was removed from the tress by passing the tress between the index and middle fingers of the hand. The tresses were placed on a tray covered with paper towels and dried overnight. Each tress was hand combed three times with the narrow teeth of an ACE® comb, and evaluated using INSTRON WET and INSTRON DRY COMBING procedures.

INSTRON procedures are standard, recognized, and industrially acceptable protocols, see for example, U.S. Pat. No. 5,389,364 (Feb. 14, 1995), U.S. Pat. No. 5,409,695 (Apr. 25, 1995), U.S. Pat. No. 5,419,627 (May 30, 1995), and U.S. Pat. No. 5,504,149 (Apr. 2, 1996).

For tests involving rinse-off conditioners, hair tresses are rinsed with tap water for 30 seconds at 40° C. The test conditioner is applied to the tress in the amount of 0.8 gram, and the tress is stroked for 30 seconds. The tress is rinsed for 30 seconds under tap water at 40° C. Excess water is removed by pulling the tress through the index and middle fingers of the hand. The tresses are allowed to dry separately on a paper towel overnight at room temperature. The tresses are combed once before performing an INSTRON study.

Test Procedure

INSTRON COMBING is an industry recognized test for determining hair conditioning by the ease of wet combing and the ease of dry combing. The test employs an INSTRON strain gauge, which is equipped to measure the force required to comb the hair. The conditioning performance is based on the ability of a particular hair treatment formulation, such as a shampoo or a hair conditioner, to reduce the force required to comb the hair with the INSTRON strain gauge. The force is reported as an Average Combing Load (ACL). The lower the number of the ACL value, the better is the conditioning effect imparted by the formulation being tested. Typically, ACL baselines are initially established using untreated tresses that have only been washed with a sodium lauryl sulfate solution. The effectiveness of a treatment can then be expressed as an ACL of the treated tress or percent reduction in ACL, calculated using the relationship:

(untreated hair ACL−treated hair ACL)×100 divided by the untreated hair ACL

According to the INSTRON WET COMBING method, hair is first wetted by dipping it into distilled water, and then the hair is detangled by combing the tress three times. The tress is then retangled by dipping in distilled water three times. Excess water is removed by passing the tress through the index and middle fingers of the hand twice. The tress is placed on a hanger and INSTRON combed. Retangling and INSTRON combing are repeated until all data points are collected. An average combing force of three tresses is measured for each treatment.

According to the INSTRON DRY COMBING method, hair is detangled by combing the tress 3 times. Then hair is retangled by swirling the tress clockwise 3 times and swirling it counter clockwise 3 times. The tress is then placed on a hanger and INSTRON combed. Retangle and Instron combing are repeated until all data points are collected. An average combing force for three tresses is measured for each treatment.

The results of INSTRON WET COMBING using Conditioners from Table 2 are shown in Table 3. The results show that all of the silicone amino polyether block copolymer emulsion containing conditioners of the present invention with the exception of D provided a reduction in wet combing force. The conditioners containing the silicone amino polyether block copolymer emulsions A and C outperformed the amino functional silicone emulsions containing conditioners and comparative silicone amino polyether block copolymer emulsion. The conditioners containing the silicone amino polyether block copolymer containing emulsions of the present invention are therefore capable of significantly improving the wet conditioning properties of hair.

The results of INSTRON DRY COMBING tests conducted with the Conditioners from Table 2 are shown in Table 4. Table 4 shows that the silicone amino polyether block copolymer containing emulsions of the present invention provided a significant reduction in dry combing force. Conditioners containing emulsions A and C showed comparable performance to the amino functional silicone emulsions and outperformed the comparative silicone amino polyether block copolymer emulsion. The conditioners containing the silicone amino polyether block copolymer containing emulsions of the present invention are therefore capable of significantly improving the dry conditioning properties of hair.

TABLE 3

INSTRON WET COMBING

| Conditioner | Average Percent Reduction |
| --- | --- |
| A | 94.7 |
| B | 42.7 |
| C | 92.5 |
| D | 2.2 |
| Nonionic Amino Siloxane Microemulsion | 58.8 |
| Cationic Amino Siloxane Emulsion | 76.3 |
| Comparative Silicone Amino Polyether Block Copolymer Emulsion | −30.1 |

TABLE 4

INSTRON DRY COMBING

| Conditioner | Average Percent Reduction |
| --- | --- |
| A | 88.4 |
| B | 65.8 |
| C | 87.1 |
| D | 66.7 |
| Nonionic Amino Siloxane Microemulsion | 81.2 |
| Cationic Amino Siloxane Emulsion | 84.8 |
| Comparative Silicone Amino Polyether Block Copolymer Emulsion | 44.9 |

Example 13

Hair Conditioner Formulations

TABLE 5

Conditioners

| Ingredient | Weight Percent | Weight Percent |
| --- | --- | --- |
| Deionized Water | q.s. to 100% | q.s. to 100% |
| Hydroxyethylcellulose[1] | 1.5 | 1.5 |
| Cetearyl Alcohol[2] | 1.0 | 1.0 |
| PEG-100 Stearate & Glyceryl Stearate[3] | 1.0 | 1.0 |
| C Emulsion[4] | 1.7 | — |
| Comparative Silicone Amino Polyether Block Copolymer Emulsion[5] | — | 4.7 |
| DMDM Hydantoin[6] | 0.2 | 0.2 |

[1]Natrosol ® 250 HHR available from Hercules of Wilmington, DE
[2]Crodocol CS-50 ® available from Croda Inc. of Edison, NJ
[3]Arlacel ® 165 available from Uniqema of Wilmington, DE
[4]C, concentration based on 1.0% active silicone level, (59.0% Active)
[5]Dow Corning ® CE 8401 Emulsion available from Dow Corning, Midland, MI, concentration based on 1.0% active silicone level (21.5% active)
[6]Glydant ® available from Lonza, Inc. of Fairlawn, NJ
Deionized water is added to the mixing vessel and heated to 75° C. With moderate agitation, the hydroxyethyl cellulose is dispersed until fully dissolved. Heat is decreased to 60° C. and cetearyl alcohol and PEG-100 stearate and glyceryl stearate is added. Heat is then decreased to 40° and the silicone silicone amino polyether block copolymer emulsion is added to the base conditioner. The conditioner is mixed for 5-10 minutes and then DMDM hydantoin is added. The water loss is compensated for and the formulation is mixed for an additional 5 minutes. The final pH of the conditioner formulations are all approximately 6-7.

The results of INSTRON WET COMBING using Conditioners from Table 5 are shown in Table 6. The results show that the silicone amino polyether block copolymer emulsion containing conditioner of the present invention provided a significant reduction in wet combing force at a lower use level. The conditioner containing 1% active silicone had similar performance to the same conditioner containing 2% active silicone from Table 2. The conditioner containing the silicone amino polyether block copolymer emulsion significantly outperformed the comparative silicone amino polyether block copolymer emulsion.

The results of INSTRON DRY COMBING tests conducted with the Conditioners from Table 5 are shown in Table 7. The results show that the silicone amino polyether block copolymer emulsion containing conditioner of the present invention provided a significant reduction in dry combing force at a lower use level. The conditioner containing 1% active silicone had similar performance to the same conditioner containing 2% active silicone from Table 2. The conditioner containing the silicone amino polyether block copolymer emulsion significantly outperformed the comparative silicone amino polyether block copolymer emulsion.

TABLE 6

INSTRON WET COMBING

| Conditioner | Average Percent Reduction |
|---|---|
| C | 89.3 |
| Comparative Silicone Amino Polyether Block Copolymer Emulsion | −33.3 |

TABLE 7

INSTRON DRY COMBING

| Conditioner | Average Percent Reduction |
|---|---|
| D | 84.5 |
| Comparative Silicone Amino Polyether Block Copolymer Emulsion | 20.2 |

Example 14

Hair Conditioner Formulations

TABLE 8

Conditioners

| Ingredient | Weight Percent | Weight Percent | Weight Percent | Weight Percent |
|---|---|---|---|---|
| Deionized Water | q.s. to 100% | q.s. to 100% | q.s. to 100% | q.s. to 100% |
| Hydroxyethylcellulose[1] | 1.5 | 1.5 | 1.5 | 1.5 |
| Cetearyl Alcohol[2] | 1.0 | 1.0 | 1.0 | 1.0 |
| PEG-100 Stearate & Glyceryl Stearate[3] | 1.0 | 1.0 | 1.0 | 1.0 |
| H Emulsion[4] | — | 2.0 | — | — |
| I Emulsion[5] | — | — | 1.8 | — |
| Comparative Silicone Amino Polyether Block Copolymer Emulsion[6] | — | — | — | 4.7 |
| DMDM Hydantoin[7] | 0.2 | 0.2 | 0.2 | 0.2 |

[1]Natrosol ® 250 HHR available from Hercules of Wilmington, DE
[2]Crodocol CS-50 ® available from Croda Inc. of Edison, NJ
[3]Arlacel ® 165 available from Uniqema of Wilmington, DE
[4]H, concentration based on 1.2% active silicone level, (59.6% Active)
[5]I, concentration based on 1.1% active silicone level, (59.3% Active)
[6]Dow Corning ® CE 8401 Emulsion available from Dow Corning, Midland, MI, concentration based on 1.0% active silicone level (21.5% active)
[7]Glydant ® available from Lonza, Inc. of Fairlawn, NJ Deionized water is added to the mixing vessel and heated to 75° C. With moderate agitation, the hydroxyethyl cellulose is dispersed until fully dissolved. Heat is decreased to 60° C. and cetearyl alcohol and PEG-100 stearate and glyceryl stearate is added. Heat is then decreased to 40° and the silicone silicone amino polyether block copolymer emulsion is added to the base conditioner. The conditioner is mixed for 5-10 minutes and then DMDM hydantoin is added. The water loss is compensated for and the formulation is mixed for an additional 5 minutes. The final pH of the conditioner formulations are all approximately 6-7.

The results of INSTRON WET COMBING using Conditioners from Table 8 are shown in Table 9. The results show that the silicone amino polyether block copolymer emulsion containing conditioners of the present invention provided a significant reduction in wet combing force. Both conditioners containing the silicone amino polyether block copolymer emulsions H and I significantly outperformed the control conditioner without silicone and comparative silicone amino polyether block copolymer emulsion. The conditioners containing the silicone amino polyether block copolymer containing emulsions of the present invention are therefore capable of significantly improving the wet conditioning properties of hair.

The results of INSTRON DRY COMBING tests conducted with the Conditioners from Table 8 are shown in Table 10. Table 10 shows that the silicone amino polyether block copolymer containing emulsions of the present invention provided a significant reduction in dry combing force. Conditioners containing emulsions H and I significantly outperformed the control conditioner without silicone and comparative silicone amino polyether block copolymer emulsion. The conditioners containing the silicone amino polyether block copolymer containing emulsions of the present invention are therefore capable of significantly improving the dry conditioning properties of hair.

TABLE 9

INSTRON WET COMBING

| Conditioner | Average Percent Reduction |
|---|---|
| Control (no silicone) | −14.0 |
| H | 85.7 |
| I | 87.7 |
| Comparative Silicone Amino Polyether Block Copolymer Emulsion | 11.4 |

TABLE 10

INSTRON DRY COMBING

| Conditioner | Average Percent Reduction |
|---|---|
| Control (no silicone) | 28.7 |
| H | 72.8 |
| I | 72.7 |
| Comparative Silicone Amino Polyether Block Copolymer Emulsion | 3.1 |

Example 15

Conditioning Shampoo Formulations

Samples of silicone amino polyether block copolymer emulsions were added to shampoo formulations using two percent by weight of the silicone polymer. The shampoo formulations are shown in Table 11. The shampoos of the present invention were prepared using A, B, C and D emulsions from Table 1. A shampoo containing a commercial nonionic amino siloxane microemulsion and comparative silicone amino SPE $(AB)_n$ copolymer emulsion were also tested for comparison purposes.

TABLE 11

Conditioning Shampoos

| Ingredient | Weight % | Weight % | Weight % | Weight % | Weight % | Weight % |
|---|---|---|---|---|---|---|
| Deionized Water | q.s. to 100% | q.s. to 100% | q.s. to 100% | q.s. to 100% | q.s. to 100% | q.s. to 100% |
| Sodium Laureth Sulfate[1] | 30 | 30 | 30 | 30 | 30 | 30 |
| Cocamide DEA[2] | 3.0 | 3.0 | 3.0 | 3.0 | 3.0 | 3.0 |
| Cocamidopropyl Betaine[3] | 7.0 | 7.0 | 7.0 | 7.0 | 7.0 | 7.0 |
| Polyquaternium-10[4] | 0.3 | 0.3 | 0.3 | 0.3 | 0.3 | 0.3 |
| PEG-150 Pentaerythrityl Tetrastearate[5] | 1.5 | 1.5 | 1.5 | 1.5 | 1.5 | 1.5 |
| A[6] | 3.3 | — | — | — | — | — |
| B[7] | — | 10.0 | — | — | — | — |
| C[8] | — | — | 3.4 | — | — | — |
| D[9] | — | — | — | 9.6 | — | — |
| Amino Siloxane Microemulsion[10] | — | — | — | — | 10.0 | — |
| Comparative Silicone Amino Polyether Block Copolymer Emulsion[11] | — | — | — | — | — | 9.3 |
| DMDM Hydantoin[12] | 0.4 | 0.4 | 0.4 | 0.4 | 0.4 | 0.4 |

[1]Standapol ES-3 ® available from Cognis Corp. of Cincinnati, OH
[2]Monamid 705 ® available from Uniqema of New Castle, DE
[3]Monateric CAB-LC ® available from Uniquema of New Castle, DE
[4]UCARE Polymer JR-30M available from Dow/Amerchol of Midland, MI
[5]Crothix ® available from Croda Inc. of Edison, NJ
[6]A, concentration based on 2% active silicone level, (60.5% Active)
[7]B, concentration based on 2% active silicone level, (20.1% Active)
[8]C, concentration based on 2% active silicone level, (59.0% Active)
[9]D, concentration based on 2% active silicone level, (20.8% Active)
[10]Dow Corning ® CE-8170 AF Microemulsion available from Dow Corning, Midland, MI, concentration based on 2% active silicone level (20% active)
[11]Dow Corning ® CE 8401 Emulsion available from Dow Corning, Midland, MI, concentration based on 2% active silicone level (21.5% active)
[12]Glydant ® available from Lonza, Inc. of Fairlawn, NJ Deionized water is added to the mixing vessel. In order to keep the active silicone loading constant throughout testing, it is necessary to adjust the water level added depending on the percent active silicone in the various emulsions used. With moderate agitation, the polyquaternium-10 is dispersed until fully dissolved. This is then heated to 75° C. and the PEG-150 pentaerythrityl tetrastearate is added with continual mixing. Heat is decreased to 40° C. and sodium lauryl ether sulfate, cocamide DEA cocamidopropyl betaine are added in that order. When completely incorporated, silicone amino polyether block copolymer emulsion is added to the base shampoo.
The shampoo is mixed for 5-10 minutes and then DMDM hydantoin is added. The water loss is compensated for and the formulation is mixed for an additional 5 minutes. The final pH of the shampoo formulations are approximately 5.5-6.0.

The results of INSTRON WET and DRY COMBING using Shampoos from Table 11 are shown in Tables 12 and 13. For wet combing, the silicone amino polyether block copolymer emulsions provided a significant reduction in wet combing force. Emulsion D demonstrated similar performance to the commercial nonionic amino siloxane microemulsion and comparative silicone amino SPE ABn copolymer emulsion. For dry combing the results show that the silicone amino polyether block copolymer emulsions C and D in the shampoo formulations provided a significant reduction in combing force and demonstrated similar performance to the commercial emulsions. Shampoo formulations containing the silicone amino polyether block copolymer emulsions are therefore capable of significantly improving the wet and dry conditioning properties of hair.

TABLE 12

INSTRON WET COMBING RESULTS

| Shampoo | Average % Reduction |
|---|---|
| A | 52.7 |
| B | 45.7 |
| C | 59.6 |
| D | 85.5 |
| Nonionic Amino Siloxane Microemulsion | 85.8 |
| Comparative Silicone Amino Polyether Block Copolymer Emulsion | 80.8 |

TABLE 13

INSTRON DRY COMBING RESULTS

| Shampoo | Average % Reduction |
|---|---|
| A | −9.7 |
| B | 13.0 |
| C | 57.0 |
| D | 67.8 |
| Nonionic Amino Siloxane Microemulsion | 48.2 |
| Comparative Silicone Amino Polyether Block Copolymer Emulsion | 50.4 |

Example 16

Conditioning Shampoo Formulations

TABLE 14

Conditioning Shampoos

| Ingredient | Weight % | Weight % | Weight % | Weight % |
|---|---|---|---|---|
| Deionized Water | q.s. to 100% | q.s. to 100% | q.s. to 100% | q.s. to 100% |
| Sodium Laureth Sulfate[1] | 30 | 30 | 30 | 30 |

TABLE 14-continued

Conditioning Shampoos

| Ingredient | Weight % | Weight % | Weight % | Weight % |
|---|---|---|---|---|
| Cocamide DEA[2] | 3.0 | 3.0 | 3.0 | 3.0 |
| Cocamidopropyl Betaine[3] | 7.0 | 7.0 | 7.0 | 7.0 |
| Polyquaternium-10[4] | 0.3 | 0.3 | 0.3 | 0.3 |
| PEG-150 Pentaerythrityl Tetrastearate[5] | 1.5 | 1.5 | 1.5 | 1.5 |
| C[6] | 1.7 | — | — | — |
| D[7] | — | 4.8 | — | — |
| Amino Siloxane Microemulsion[8] | — | — | 5.0 | — |
| Comparative Silicone Amino Polyether Block Copolymer Emulsion[9] | — | — | — | 4.7 |
| DMDM Hydantoin[10] | 0.4 | 0.4 | 0.4 | 0.4 |

[1]Standapol ES-3 ® available from Cognis Corp. of Cincinnati, OH
[2]Monamid 705 ® available from Uniqema of New Castle, DE
[3]Monateric CAB-LC ® available from Uniquema of New Castle, DE
[4]UCARE Polymer JR-30M available from Dow/Amerchol of Midland, MI
[5]Crothix ® available from Croda Inc. of Edison, NJ
[6]C, concentration based on 1% active silicone level, (59.0% Active)
[7]D, concentration based on 1% active silicone level, (20.8% Active)
[8]Dow Corning ® CE-8170 AF Microemulsion available from Dow Corning, Midland, MI, concentration based on 1% active silicone level (20% active)
[9]Dow Corning ® CE 8401 Emulsion available from Dow Corning, Midland, MI, concentration based on 1% active silicone level (21.5% active)
[10]Glydant ® available from Lonza, Inc. of Fairlawn, NJ Deionized water is added to the mixing vessel. In order to keep the active silicone loading constant throughout testing, it is necessary to adjust the water level added depending on the percent active silicone in the various emulsions used. With moderate agitation, the polyquaternium-10 is dispersed until fully dissolved. This is then heated to 75° C. and the PEG-150 pentaerythrityl tetrastearate is added with continual mixing. Heat is decreased to 40° C. and sodium lauryl ether sulfate, cocamide DEA cocamidopropyl betaine are added in that order. When completely incorporated, silicone amino polyether block copolymer emulsion is added to the base shampoo.
The shampoo is mixed for 5-10 minutes and then DMDM hydantoin is added. The water loss is compensated for and the formulation is mixed for an additional 5 minutes. The final pH of the shampoo formulations are approximately 5.5-6.0.

The results of INSTRON WET and DRY COMBING using Shampoos from Table 14 are shown in Tables 15 and 16. The active silicone content was decreased from 2 to 1% for this evaluation. For wet combing, the silicone amino polyether block copolymer emulsions provided a significant reduction in wet combing force. Emulsions C and D demonstrated better performance than the nonionic amino silicone microemulsion, but less than the comparative silicone amino polyether block copolymer emulsion. The dry combing results for the silicone amino polyether block copolymer emulsions in the shampoo formulations provided a more significant reduction in combing force compared to both the amino silicone microemulsion and the comparative silicone amino polyether block copolymer emulsion. Shampoo formulations containing the silicone amino polyether block copolymer emulsions are therefore capable of significantly improving the wet and dry conditioning properties of hair at low use levels.

TABLE 15

INSTRON WET COMBING RESULTS

| Shampoo | Average % Reduction |
|---|---|
| C | 78.5 |
| D | 77.4 |
| Nonionic Amino Siloxane Microemulsion | 67.6 |
| Comparative Silicone Amino Polyether Block Copolymer Emulsion | 86.9 |

TABLE 16

INSTRON DRY COMBING RESULTS

| Shampoo | Average % Reduction |
|---|---|
| C | 70.4 |
| D | 64.8 |
| Nonionic Amino Siloxane Microemulsion | 53.6 |
| Comparative Silicone Amino Polyether Block Copolymer Emulsion | 42.3 |

Example 17

Conditioning Shampoo Formulations

TABLE 17

Conditioning Shampoos

| Ingredient | Weight % | Weight % | Weight % | Weight % | Weight % |
|---|---|---|---|---|---|
| Deionized Water | q.s. to 100% | q.s. to 100% | q.s. to 100% | q.s. to 100% | q.s. to 100% |
| Sodium Laureth Sulfate[1] | 30 | 30 | 30 | 30 | 30 |
| Cocamide DEA[2] | 3.0 | 3.0 | 3.0 | 3.0 | 3.0 |
| Cocamidopropyl Betaine[3] | 7.0 | 7.0 | 7.0 | 7.0 | 7.0 |
| Polyquaternium-10[4] | 0.3 | 0.3 | 0.3 | 0.3 | 0.3 |
| PEG-150 Pentaerythrityl Tetrastearate[5] | 1.5 | 1.5 | 1.5 | 1.5 | 1.5 |
| D[6] | 5.0 | — | — | — | — |
| E[7] | — | 5.1 | — | — | — |
| F[8] | — | — | 5.0 | — | — |
| G[9] | — | — | — | 5.0 | — |
| Comparative Silicone Amino Polyether Block Copolymer Emulsion[10] | — | — | — | — | 4.7 |
| DMDM Hydantoin[11] | 0.4 | 0.4 | 0.4 | 0.4 | 0.4 |

[1]Standapol ES-3 ® available from Cognis Corp. of Cincinnati, OH
[2]Monamid 705 ® available from Uniqema of New Castle, DE
[3]Monateric CAB-LC ® available from Uniquema of New Castle, DE
[4]UCARE Polymer JR-30M available from Dow/Amerchol of Midland, MI
[5]Crothix ® available from Croda Inc. of Edison, NJ
[6]D, concentration based on 1% active silicone level, (20.8% Active)
[7]E, concentration based on 1% active silicone level, (19.7% Active)
[8]F, concentration based on 1% active silicone level, (20.3% Active)
[9]G, concentration based on 1% active silicone level, (20.1% Active)
[10]Dow Corning ® CE 8401 Emulsion available from Dow Corning, Midland, MI, concentration based on 1% active silicone level (21.5% active)
[11]Glydant ® available from Lonza, Inc. of Fairlawn, NJ Deionized water is added to the mixing vessel. In order to keep the active silicone loading constant throughout testing, it is necessary to adjust the water level added depending on the percent active silicone in the various emulsions used. With moderate agitation, the polyquaternium-10 is dispersed until fully dissolved. This is then heated to 75° C. and the PEG-150 pentaerythrityl tetrastearate is added with continual mixing. Heat is decreased to 40° C. and sodium lauryl ether sulfate, cocamide DEA cocamidopropyl betaine are added in that order. When completely incorporated, silicone amino polyether block copolymer emulsion is added to the base shampoo. The shampoo is mixed for 5-10 minutes and then DMDM hydantoin is added. The water loss is compensated for and the formulation is mixed for an additional 5 minutes. The final pH of the shampoo formulations are approximately 5.5-6.0.

The results of INSTRON WET and DRY COMBING using Shampoos from Table 17 are shown in Tables 18 and 19. For wet combing, the silicone amino polyether block copolymer emulsions provided a significant reduction in wet combing force and demonstrated similar performance to the comparative silicone amino polyether block copolymer emulsion. The dry combing results showed the silicone amino polyether block copolymer emulsions in the shampoo formulations provided a significant reduction in combing force and provided better performance than the comparative silicone amino polyether block copolymer emulsion. Shampoo formulations containing the silicone amino polyether block copolymer emulsions are therefore capable of significantly improving the wet and dry conditioning properties of hair.

TABLE 18

INSTRON WET COMBING RESULTS

| Shampoo | Average % Reduction |
|---|---|
| D | 78.6 |
| E | 72.1 |
| F | 82.7 |
| G | 81.3 |
| Comparative Silicone Amino Polyether Block Copolymer Emulsion | 87.3 |

TABLE 19

INSTRON DRY COMBING RESULTS

| Shampoo | Average % Reduction |
|---|---|
| D | 69.6 |
| E | 72.4 |
| F | 73.7 |
| G | 75.2 |
| Comparative Silicone Amino Polyether Block Copolymer Emulsion | 59.8 |

Example 18

Conditioning Shampoo Formulations

TABLE 20

Conditioning Shampoos

| Ingredient | Weight % | Weight % | Weight % | Weight % |
|---|---|---|---|---|
| Deionized Water | q.s. to 100% | q.s. to 100% | q.s. to 100% | q.s. to 100% |
| Sodium Laureth Sulfate[1] | 30 | 30 | 30 | 30 |
| Cocamide DEA[2] | 3.0 | 3.0 | 3.0 | 3.0 |
| Cocamidopropyl Betaine[3] | 7.0 | 7.0 | 7.0 | 7.0 |
| Polyquaternium-10[4] | 0.3 | 0.3 | 0.3 | 0.3 |
| PEG-150 Pentaerythrityl Tetrastearate[5] | 1.5 | 1.5 | 1.5 | 1.5 |
| H[6] | — | 2.0 | — | — |
| I[7] | — | — | 1.8 | — |
| Comparative Silicone Amino Polyether Block Copolymer Emulsion[8] | — | — | — | 4.7 |
| DMDM Hydantoin[9] | 0.4 | 0.4 | 0.4 | 0.4 |

[1]Standapol ES-3 ® available from Cognis Corp. of Cincinnati, OH
[2]Monamid 705 ® available from Uniqema of New Castle, DE
[3]Monateric CAB-LC ® available from Uniquema of New Castle, DE
[4]UCARE Polymer JR-30M available from Dow/Amerchol of Midland, MI
[5]Crothix ® available from Croda Inc. of Edison, NJ
[6]H, concentration based on 1.2% active silicone level, (59.6% Active)
[7]I, concentration based on 1.1% active silicone level, (59.3% Active)
[8]Dow Corning ® CE 8401 Emulsion available from Dow Corning, Midland, MI, concentration based on 1.0% active silicone level (21.5% active)
[9]Glydant ® available from Lonza, Inc. of Fairlawn, NJ TABLE 20-continued Conditioning Shampoos

| Ingredient | Weight % | Weight % | Weight % | Weight % |
|---|---|---|---|---|

Deionized water is added to the mixing vessel. In order to keep the active silicone loading constant throughout testing, it is necessary to adjust the water level added depending on the percent active silicone in the various emulsions used. With moderate agitation, the polyquaternium-10 is dispersed until fully dissolved. This is then heated to 75° C. and the PEG-150 pentaerythrityl tetrastearate is added with continual mixing. Heat is decreased to 40° C. and sodium lauryl ether sulfate, cocamide DEA cocamidopropyl betaine are added in that order. When completely incorporated, silicone amino polyether block copolymer emulsion is added to the base shampoo. The shampoo is mixed for 5-10 minutes and then DMDM hydantoin is added. The water loss is compensated for and the formulation is mixed for an additional 5 minutes. The final pH of the shampoo formulations are approximately 5.5-6.0.

The results of INSTRON WET and DRY COMBING using Shampoos from Table 20 are shown in Tables 21 and 22. For wet combing, the silicone amino polyether block copolymer emulsions provided a significant reduction in wet combing force and demonstrated significant improvement over the control shampoo without silicone and similar performance to the comparative silicone amino polyether block copolymer emulsion. The dry combing results showed the silicone amino polyether block copolymer emulsions in the shampoo formulations provided a significant reduction in combing force and demonstrated significant improvement over the control shampoo without silicone. Shampoo containing emulsion I provided better performance than the comparative silicone amino polyether block copolymer emulsion. Shampoo formulations containing the silicone amino polyether block copolymer emulsions are therefore capable of significantly improving the wet and dry conditioning properties of hair.

TABLE 21

INSTRON WET COMBING RESULTS

| Shampoo | Average % Reduction |
|---|---|
| Control (no silicone) | 27.5 |
| H | 72.2 |
| I | 83.3 |
| Comparative Silicone Amino Polyether Block Copolymer Emulsion | 87.6 |

TABLE 22

INSTRON DRY COMBING RESULTS

| Shampoo | Average % Reduction |
|---|---|
| Control (no silicone) | −16.2 |
| H | 45.0 |
| I | 78.1 |
| Comparative Silicone Amino Polyether Block Copolymer Emulsion | 65.5 |

Hair Sensory

Sensory testing was performed using conditioner formulations containing the silicone amino polyether block copolymer emulsions of the present invention, a comparative silicone amino polyether block copolymer emulsion, a nonionic amino siloxane microemulsion and control conditioner without silicone. The formulations used for the testing are in Table 23. The testing was performed using the terms defined in ASTM Standard E 2082-00 (Standard Guide for Descriptive Analysis of Shampoo Performance). A ranking is given from 1-5, where 1 is the least and 5 is the most of the specified parameter. The wet and dry sensory results are reported in Tables 24 and 25, respectively. The wet sensory results show that the silicone amino polyether block copolymer emulsions provided significant wet sensory benefits, specifically ease of detangling, slipperiness and combability over the control conditioner without silicone, nonionic amino siloxane microemulsion and comparative silicone amino polyether block copolymer emulsion. The dry sensory results show that the silicone amino polyether block copolymer emulsions provided significant dry sensory benefits, specifically ease of detangling, pliability, smoothness and combability over the control conditioner without silicone, nonionic amino siloxane microemulsion and comparative silicone amino polyether block copolymer emulsion.

TABLE 23

Conditioners

| Ingredient | Weight Percent | Weight Percent | Weight Percent | Weight Percent |
|---|---|---|---|---|
| Deionized Water | q.s. to 100% | q.s. to 100% | q.s. to 100% | q.s. to 100% |
| Hydroxyethylcellulose[1] | 1.5 | 1.5 | 1.5 | 1.5 |
| Cetearyl Alcohol[2] | 1.0 | 1.0 | 1.0 | 1.0 |
| PEG-100 Stearate & Glyceryl Stearate[3] | 1.0 | 1.0 | 1.0 | 1.0 |
| C Emulsion[4] | — | 1.7 | — | — |
| Comparative Silicone Amino Polyether Block Copolymer Emulsion[5] | — | — | 4.7 | — |
| Nonionic Amino Siloxane Microemulsion[6] | — | — | — | 5.0 |
| DMDM Hydantoin[7] | 0.2 | 0.2 | 0.2 | 0.2 |

[1]Natrosol ® 250 HHR available from Hercules of Wilmington, DE
[2]Crodocol CS-50 ® available from Croda Inc. of Edison, NJ
[3]Arlacel ® 165 available from Uniqema of Wilmington, DE
[4]C, concentration based on 1.0% active silicone level, (59.0% Active)
[5]Dow Corning ® CE 8401 Emulsion available from Dow Corning, Midland, MI, concentration based on 1.0% active silicone level (21.5% active)
[6]Dow Corning ® CE-8170 AF Microemulsion available from Dow Corning, Midland, MI, concentration based on 1% active silicone level (20% active)
[7]Glydant ® available from Lonza, Inc. of Fairlawn, NJ
Deionized water is added to the mixing vessel and heated to 75° C. With moderate agitation, the hydroxyethyl cellulose is dispersed until fully dissolved. Heat is decreased to 60° C. and cetearyl alcohol and PEG-100 stearate and glyceryl stearate is added. Heat is then decreased to 40° and the silicone silicone amino polyether block copolymer emulsion is added to the base conditioner. The conditioner is mixed for 5-10 minutes and then DMDM hydantoin is added. The water loss is compensated for and the formulation is mixed for an additional 5 minutes. The final pH of the conditioner formulations are all approximately 6-7.

TABLE 24

Wet Sensory Results

| Conditioner | Ease of Detangling | Slipperiness | Combability |
|---|---|---|---|
| Emulsion C | 5 | 5 | 5 |
| Comparative Silicone Amino Polyether Block Copolymer Emulsion | 3 | 2 | 3 |
| Nonionic Amino Siloxane Microemulsion | 4 | 3 | 4 |
| Control Conditioner (no silicone) | 2 | 2 | 2 |

TABLE 25

Dry Sensory Results

| Conditioner | Ease of Detangling | Pliability | Smoothness | Combability | Static |
|---|---|---|---|---|---|
| Emulsion C | 5 | 5 | 5 | 5 | 3 |
| Comparative Silicone Amino Polyether Block Copolymer Emulsion | 2 | 3 | 4 | 2 | 3 |
| Nonionic Amino Siloxane Microemulsion | 3 | 4 | 3 | 3 | 2 |
| Control Conditioner (no silicone) | 2 | 3 | 2 | 2 | 5 |

Wet and dry sensory performance was tested using conditioners from Table 8. The wet and dry sensory results are reported in Tables 26 and 27, respectively. The sensory results in Table 26 show that the silicone amino polyether block copolymer emulsions provided significant wet sensory benefits over the control conditioner without silicone and the comparative silicone amino polyether block copolymer emulsion for ease of detangling, slipperiness and combability. The sensory results in Table 27 show that the silicone amino polyether block copolymer emulsions provided significant dry sensory benefits over the control conditioner without silicone and the comparative silicone amino polyether block copolymer emulsion for ease of detangling, pliability, smoothness, combability and less static.

TABLE 26

Wet Sensory Results

| Conditioner | Ease of Detangling | Slipperiness | Combability |
|---|---|---|---|
| Emulsion H | 4 | 4 | 4 |
| Emulsion I | 5 | 5 | 5 |
| Comparative Silicone Amino Polyether Block Copolymer Emulsion | 1 | 2 | 2 |
| Control Conditioner (no silicone) | 1 | 1 | 1 |

TABLE 27

Dry Sensory Results

| Conditioner | Ease of Detangling | Pliability | Smoothness | Combability | Static |
|---|---|---|---|---|---|
| Emulsion H | 4 | 4 | 4 | 4 | 1 |
| Emulsion I | 4 | 4 | 4 | 4 | 1 |
| Comparative Silicone Amino Polyether Block Copolymer Emulsion | 2 | 3 | 2 | 1 | 3 |
| Control Conditioner (no silicone) | 2 | 2 | 2 | 1 | 3 |

Sensory testing was performed using shampoo formulations containing the silicone amino polyether block copolymer emulsions of the present invention, a comparative silicone amino polyether block copolymer emulsion, a nonionic amino siloxane microemulsion and control shampoo without silicone. The formulations used for the testing are from Table 14. The wet and dry sensory results are reported in Tables 28 and 29, respectively. The sensory results show that the silicone amino polyether block copolymer emulsions provided significant wet sensory benefits, ease of detangling, slipperiness and combability over the control shampoo without silicone and shampoo containing the nonionic amino siloxane microemulsion and had similar performance to the comparative silicone amino polyether block copolymer emulsion. The sensory results show that the silicone amino polyether block copolymer emulsions provided significant dry sensory benefits, ease of detangling, pliability, smoothness, combability and less static over the control shampoo without silicone and shampoo containing the nonionic amino siloxane microemulsion and had similar performance to the comparative silicone amino polyether block copolymer emulsion.

TABLE 28

Wet Sensory Results

| Shampoo | Ease of Detangling | Slipperiness | Combability |
|---|---|---|---|
| Emulsion C | 5 | 5 | 4 |
| Comparative Silicone Amino Polyether Block Copolymer Emulsion | 4 | 5 | 4 |
| Nonionic Amino Siloxane Microemulsion | 4 | 4 | 3 |
| Control Conditioner (no silicone) | 2 | 3 | 2 |

TABLE 29

Dry Sensory Results

| Shampoo | Ease of Detangling | Pliability | Smoothness | Combability | Static |
|---|---|---|---|---|---|
| Emulsion C | 5 | 5 | 5 | 5 | 2 |
| Comparative Silicone Amino Polyether Block Copolymer Emulsion | 5 | 4 | 5 | 4 | 3 |
| Nonionic Amino Siloxane Microemulsion | 4 | 3 | 3 | 3 | 3 |
| Control Conditioner (no silicone) | 2 | 1 | 2 | 2 | 5 |

Wet and dry sensory testing was also performed on shampoos from Table 20. The wet and dry sensory results are reported in Tables 30 and 31, respectively. The overall sensory results show the silicone amino polyether block copolymer emulsions provided significant wet and dry sensory benefits over the control shampoo without silicone and similar performance to the comparative silicone amino polyether block copolymer emulsion.

TABLE 30

Wet Sensory Results

| Shampoo | Ease of Detangling | Slipperiness | Combability |
|---|---|---|---|
| Emulsion H | 4 | 3 | 4 |
| Emulsion I | 4 | 4 | 4 |
| Comparative Silicone Amino Polyether Block Copolymer Emulsion | 5 | 4 | 5 |
| Control Conditioner (no silicone) | 2 | 1 | 2 |

TABLE 31

Dry Sensory Results

| Shampoo | Ease of Detangling | Pliability | Smoothness | Combability | Static |
|---|---|---|---|---|---|
| Emulsion H | 3 | 4 | 4 | 3 | 2 |
| Emulsion I | 4 | 4 | 4 | 4 | 2 |
| Comparative Silicone Amino Polyether Block Copolymer Emulsion | 4 | 4 | 4 | 4 | 2 |
| Control Conditioner (no silicone) | 2 | 2 | 2 | 2 | 2 |

Curl Retention

Test Procedure

CURL RETENTION is an industry recognized test for determining hair styling and hold properties by subjecting curled hair tresses to constant temperature and humidity conditions for a specified period of time. Curl retention is measured by recording the difference in length of curled hair tresses before and during high humidity and constant temperature conditions. Already prepared natural virgin brown round hair tresses weighing 2 gram and measuring 25 cm long are employed. To pre-treat all of the tresses, 1.0 gram of a solution containing nine percent of sodium lauryl sulfate is applied and lathered through each tress for 30 seconds. Each tress is rinsed for 30 seconds under running water. Excess water is removed from each tress by passing the tress between the index and middle fingers of the hand. The tresses are placed on a tray covered with paper towels and dried overnight. Each tress is hand combed three times with the narrow teeth of a comb. Each tress is then wet for 15 seconds under tap water at 37° C. and the excess water is removed by pulling the tress through the index and middle fingers of the hand.

Then each of the tresses is treated with either 500 microliters of a 2% active silicone amino polyether block copolymer emulsion. Each tress is curled around a ¼" spiral perm rod and dried in a 40° C. oven overnight. The tresses are removed from the rod, keeping the curl intact and hung in a humidity chamber. The conditions of the humidity chamber are 25° C. and 70% relative humidity. The tress lengths are then measured periodically over 5 hours. Following the test, the maximum tress length is measured by unrolling it completely. An average of two tresses is measured for each treatment. The percent curl retention is calculated using the relationship:

(maximum tress length−tress length at specific time)/
(maximum tress length−tress length at time=0)
·100

Example 19

Leave-On Conditioner Application

Silicone amino polyether block copolymer emulsions of the present invention were further diluted to a 2% active concentration of silicone copolymer, and 500 microliters of each of the diluted emulsions was applied to hair tresses for curl retention testing. The curl retention results are shown in Table 32.

TABLE 32

Curl Retention - Silicone Amino Polyether
Block Copolymer Emulsion 2% Active Dilution

| Treatment | Curl Retention (%) after 5 hrs | Observations |
|---|---|---|
| Deionized Water | 34 | Resistance to combing; rough; minimum bounce |
| C | 42 | Easy to comb; smooth; good bounce |
| D | 35 | Easy to comb; smooth; good bounce |
| Silicone Amino Elastomer Emulsion | 42 | Easy to comb; smooth; good bounce |

The results in Table 32 demonstrate that the silicone amino polyether block copolymer emulsion C provided flexible hold and styling benefits, in addition to imparting a nice soft feel to the hair. Even when the tresses were stretched or combed to remove the curl, they were observed to bounce right back to their original shaped curl. The tresses treated with Emulsion C provided similar performance to a silicone amino elastomer emulsion developed for flexible styling benefits.

The invention claimed is:

1. A personal care composition comprising a silicone polyether copolymer having an average formula $$A\text{-}R_2SiO(R_2SiO)_xSiR_2\text{---}[[R^1O(C_mH_{2m}O)_yR^1][R_2SiO(R_2SiO)_x]R_2Si]_n\text{-}A$$

where
  A is an aminofunctional endblocking group of the formula $R^4CH_2CH(OH)CH_2OR^2\text{---}$
    wherein $R^4$ is an aminofunctional group,
  $R^2$ is a divalent hydrocarbon linking group containing 2 to 6 carbon atoms
  x is $\geq 0$, m is from 2 to 4 inclusive, y is $\geq 4$, n is $\geq 1$,
  R is independently a monovalent hydrocarbon group containing 1 to 30 carbons,
  $R^1$ is a divalent hydrocarbon containing 2 to 30 carbons.

2. The personal care composition of claim 1 wherein $R^4$ has a formula selected from $H(R^3)N\text{---}$, $(R^3)_2N\text{---}$, and $(R^3)_3N\text{---}$, where $R^3$ is independently a monovalent organic group containing 1 to 30 carbon atoms.

3. The personal care composition of claim 2 wherein $R^4$ is $(CH_3)HN\text{---}$, $(CH_3)_2N\text{---}$, $(CH_3CH_2)HN\text{---}$, $(CH_3CH_2)_2N\text{---}$, $(HOCH_2CH_2)_2N\text{---}$, piperazine, or $[CH_2CH(OH)CH_3]_2N\text{---}$.

4. The personal care composition of claim 1 wherein the silicone polyether copolymer is in an emulsion.

5. The composition of claim 1 wherein the personal care composition is selected from a shampoo, a hair conditioner, a hair fixative, a hair styling aid, a hair colorant, a hair relaxer, a shower gel, a skin moisturizer, a skin conditioner, a body conditioner, color cosmetic, a lipstick, a foundation, a sun protection product, an antiperspirant, and a deodorant.

6. A method of treating hair comprising apply to hair a personal care composition comprising a silicone polyether copolymer having an average formula $$A\text{-}R_2SiO(R_2SiO)_xSiR_2\text{---}[[R^1O(C_mH_{2m}O)_yR^1][R_2SiO(R_2SiO)_x]R_2Si]_n\text{-}A$$

where
  A is an aminofunctional endblocking group of the formula $R^4CH_2CH(OH)CH_2OR^2\text{---}$
    wherein $R^4$ is an aminofunctional group,
  $R^2$ is a divalent hydrocarbon linking group containing 2 to 6 carbon atoms
  x is $\geq 0$, m is from 2 to 4 inclusive, y is $\geq 4$, n is $\geq 1$,
  R is independently a monovalent hydrocarbon group containing 1 to 30 carbons,
  $R^1$ is a divalent hydrocarbon containing 2 to 30 carbons.

* * * * *